(12) United States Patent
Okazaki et al.

(10) Patent No.: US 8,900,123 B2
(45) Date of Patent: Dec. 2, 2014

(54) ENDOSCOPY METHOD AND ENDOSCOPE

(75) Inventors: Yoshiro Okazaki, Tokyo (JP);
Michihiro Sugahara, Tokyo (JP)

(73) Assignee: Olympus Corporation, Tokyo (JP)

( * ) Notice: Subject to any disclaimer, the term of this patent is extended or adjusted under 35 U.S.C. 154(b) by 900 days.

(21) Appl. No.: 12/714,827

(22) Filed: Mar. 1, 2010

(65) Prior Publication Data

US 2010/0240952 A1     Sep. 23, 2010

Related U.S. Application Data

(60) Provisional application No. 61/244,586, filed on Sep. 22, 2009.

(30) Foreign Application Priority Data

Mar. 2, 2009   (JP) ................................. 2009-048460
Dec. 16, 2009  (JP) ................................. 2009-285073

(51) Int. Cl.
| | |
|---|---|
| A61B 1/00 | (2006.01) |
| A61B 1/05 | (2006.01) |
| A61B 17/34 | (2006.01) |
| A61M 25/10 | (2013.01) |
| A61B 17/02 | (2006.01) |
| A61B 17/00 | (2006.01) |
| A61M 25/04 | (2006.01) |
| A61B 17/30 | (2006.01) |
| A61B 18/00 | (2006.01) |

(52) U.S. Cl.
CPC .... *A61M 25/1011* (2013.01); *A61B 2017/3488* (2013.01); *A61M 2025/1047* (2013.01); *A61B 2017/0243* (2013.01); *A61B 2017/00247* (2013.01); *A61M 25/04* (2013.01); *A61B 1/05* (2013.01); *A61B 1/0008* (2013.01); *A61B 2017/308* (2013.01); *A61B 17/0218* (2013.01); *A61B 1/00082* (2013.01); *A61M 2025/1052* (2013.01); *A61B 1/00177* (2013.01); *A61B 2018/00392* (2013.01)
USPC ........................................................ 600/102

(58) Field of Classification Search
USPC .................................................. 600/102, 174
See application file for complete search history.

(56) References Cited

U.S. PATENT DOCUMENTS

| 3,281,141 A | 10/1966 | Smiley et al. |
| 3,859,985 A | 1/1975 | Eckhart |

(Continued)

FOREIGN PATENT DOCUMENTS

| FR | 2 914 840 | 10/2008 |
| JP | 62-035318 | 2/1987 |

(Continued)

OTHER PUBLICATIONS

Sosa et al., "A New Technique to Perform Epicardial Mapping in the Electrophysiology Laboratory", Journal of Cardiovascular Electrophysiology, Apr. 29, 2007, pp. 531-536, vol. 7, Issue 6.

(Continued)

*Primary Examiner* — Clayton E Laballe
*Assistant Examiner* — Linda B Smith
(74) *Attorney, Agent, or Firm* — Scully, Scott, Murphy & Presser, P.C.

(57) ABSTRACT

With an endoscope including a long, thin inserted portion that is inserted into the body of a patient, securing means for securing the inserted portion to tissue inside the body, the securing means being provided at least at a distal-end portion of the inserted portion, an observation optical system that is provided at the inserted portion and that acquires an image of the tissue, and observation-distance adjusting means for adjusting the distance between the observation optical system and a surface of the tissue, it is possible to attain a stable field of view without having to stop the pulsation or the like of the heart or other tissue.

40 Claims, 26 Drawing Sheets

(56) References Cited

U.S. PATENT DOCUMENTS

| | | | |
|---|---|---|---|
| 4,063,553 A | 12/1977 | Karsh | |
| 4,224,929 A * | 9/1980 | Furihata | 600/116 |
| 4,319,568 A | 3/1982 | Tregoning | |
| 4,829,448 A | 5/1989 | Balding et al. | |
| 4,884,567 A | 12/1989 | Elliott et al. | |
| 4,991,603 A | 2/1991 | Cohen et al. | |
| 5,035,231 A | 7/1991 | Kubokawa et al. | |
| 5,048,537 A | 9/1991 | Messinger | |
| 5,297,536 A | 3/1994 | Wilk | |
| 5,309,896 A | 5/1994 | Moll et al. | |
| 5,324,266 A | 6/1994 | Ambrisco et al. | |
| 5,336,252 A | 8/1994 | Cohen | |
| 5,400,773 A * | 3/1995 | Zhu et al. | 600/207 |
| 5,549,569 A | 8/1996 | Lynn et al. | |
| 5,697,916 A | 12/1997 | Schraga | |
| 5,725,525 A | 3/1998 | Kordis | |
| 5,735,791 A | 4/1998 | Alexander, Jr. et al. | |
| 5,759,150 A | 6/1998 | Konou et al. | |
| 5,968,017 A | 10/1999 | Lampropoulos et al. | |
| 6,015,382 A | 1/2000 | Zwart et al. | |
| 6,017,332 A | 1/2000 | Urrutia | |
| 6,071,295 A | 6/2000 | Takahashi | |
| 6,203,490 B1 | 3/2001 | Krajicek | |
| 6,251,093 B1 | 6/2001 | Valley et al. | |
| 6,267,717 B1 | 7/2001 | Stoll et al. | |
| 6,338,710 B1 | 1/2002 | Takahashi et al. | |
| 6,371,910 B1 | 4/2002 | Zwart et al. | |
| 6,390,976 B1 | 5/2002 | Spence et al. | |
| 6,471,644 B1 * | 10/2002 | Sidor, Jr. | 600/204 |
| 6,478,029 B1 | 11/2002 | Boyd et al. | |
| 6,699,259 B2 | 3/2004 | Fogarty et al. | |
| 6,701,930 B2 | 3/2004 | Benetti et al. | |
| 6,705,988 B2 | 3/2004 | Spence et al. | |
| 6,706,013 B1 | 3/2004 | Bhat et al. | |
| 6,740,082 B2 | 5/2004 | Shadduck | |
| 6,743,169 B1 | 6/2004 | Taylor et al. | |
| 6,890,295 B2 | 5/2005 | Michels et al. | |
| 7,022,118 B2 * | 4/2006 | Ariura et al. | 606/10 |
| 7,229,408 B2 | 6/2007 | Douglas et al. | |
| 7,394,976 B2 | 7/2008 | Entenman et al. | |
| 7,398,781 B1 | 7/2008 | Chin | |
| 7,399,272 B2 | 7/2008 | Kim et al. | |
| 7,485,624 B2 | 2/2009 | Donovan | |
| 7,621,867 B2 | 11/2009 | Kura et al. | |
| 7,914,444 B2 | 3/2011 | Moriyama et al. | |
| 8,002,802 B2 | 8/2011 | Abdou | |
| 8,109,903 B2 * | 2/2012 | Terliuc et al. | 604/96.01 |
| 8,246,539 B2 | 8/2012 | Hjelle et al. | |
| 8,409,078 B2 * | 4/2013 | Ikeda | 600/116 |
| 8,480,569 B2 * | 7/2013 | Terliuc et al. | 600/153 |
| 8,523,762 B2 * | 9/2013 | Miyamoto et al. | 600/116 |
| 2002/0010388 A1 | 1/2002 | Taylor et al. | |
| 2002/0099270 A1 | 7/2002 | Taylor et al. | |
| 2004/0064138 A1 | 4/2004 | Grabek | |
| 2004/0153098 A1 * | 8/2004 | Chin et al. | 606/129 |
| 2004/0230099 A1 | 11/2004 | Taylor et al. | |
| 2005/0049463 A1 | 3/2005 | Arai et al. | |
| 2005/0065409 A1 | 3/2005 | de la Torre et al. | |
| 2005/0159645 A1 | 7/2005 | Bertolero et al. | |
| 2005/0209506 A1 | 9/2005 | Butler et al. | |
| 2006/0155169 A1 * | 7/2006 | Bastia et al. | 600/199 |
| 2006/0200002 A1 | 9/2006 | Guenst | |
| 2006/0259017 A1 * | 11/2006 | Heil et al. | 606/1 |
| 2006/0287577 A1 | 12/2006 | Wendlandt | |
| 2006/0293662 A1 | 12/2006 | Boyer, II et al. | |
| 2007/0023334 A1 | 2/2007 | Hallstadius et al. | |
| 2007/0088203 A1 | 4/2007 | Lau | |
| 2007/0135686 A1 | 6/2007 | Pruitt, Jr. et al. | |
| 2007/0255100 A1 | 11/2007 | Barlow et al. | |
| 2008/0015569 A1 * | 1/2008 | Saadat et al. | 606/41 |
| 2008/0033467 A1 * | 2/2008 | Miyamoto et al. | 606/180 |
| 2008/0096165 A1 | 4/2008 | Virnicchi et al. | |
| 2008/0167621 A1 | 7/2008 | Wagner et al. | |
| 2008/0275371 A1 | 11/2008 | Hoffmann | |
| 2009/0043166 A1 * | 2/2009 | Ishii | 600/130 |
| 2009/0054943 A1 | 2/2009 | Qu et al. | |
| 2009/0171152 A1 * | 7/2009 | Aoki et al. | 600/114 |
| 2009/0299364 A1 * | 12/2009 | Batchelor et al. | 606/41 |
| 2009/0318759 A1 | 12/2009 | Jacobsen et al. | |
| 2010/0041949 A1 * | 2/2010 | Tolkowsky | 600/109 |
| 2010/0145361 A1 * | 6/2010 | Francischelli et al. | 606/139 |
| 2010/0191164 A1 | 7/2010 | Sasaki et al. | |
| 2010/0268029 A1 | 10/2010 | Phan et al. | |
| 2010/0317925 A1 * | 12/2010 | Banchieri et al. | 600/210 |
| 2011/0082452 A1 * | 4/2011 | Melsky et al. | 606/15 |
| 2011/0144572 A1 | 6/2011 | Kassab et al. | |
| 2011/0261353 A1 * | 10/2011 | Teramura | 356/213 |
| 2012/0277538 A1 | 11/2012 | Okada | |
| 2012/0277796 A1 | 11/2012 | Gabelberger et al. | |
| 2012/0283766 A1 * | 11/2012 | Makower et al. | 606/192 |
| 2013/0012782 A1 | 1/2013 | Stearns et al. | |

FOREIGN PATENT DOCUMENTS

| | | |
|---|---|---|
| JP | 64-20836 | 1/1989 |
| JP | 2-55960 | 4/1990 |
| JP | 6507810 A | 9/1994 |
| JP | 7501959 A | 3/1995 |
| JP | 7-265321 | 10/1995 |
| JP | 8-117232 | 5/1996 |
| JP | 08-280815 | 10/1996 |
| JP | 975353 A | 3/1997 |
| JP | 9-187415 | 7/1997 |
| JP | 10234738 A | 9/1998 |
| JP | 11-276422 | 10/1999 |
| JP | 200023988 A | 1/2000 |
| JP | 2000-176011 | 6/2000 |
| JP | 2001-519212 | 10/2001 |
| JP | 2001-340462 | 12/2001 |
| JP | 2002-017854 | 1/2002 |
| JP | 2002-522116 | 7/2002 |
| JP | 2003-144378 | 5/2003 |
| JP | 2003529390 A | 10/2003 |
| JP | 2004-33525 | 2/2004 |
| JP | 2004-81852 | 3/2004 |
| JP | 2004-097391 | 4/2004 |
| JP | 2004-105226 | 4/2004 |
| JP | 2006-271831 | 10/2006 |
| JP | 2007-054333 | 3/2007 |
| JP | 2007-505680 | 3/2007 |
| JP | 3143693 | 7/2008 |
| JP | 2008-540117 | 11/2008 |
| WO | 9221295 A1 | 12/1992 |
| WO | 9309722 A1 | 5/1993 |
| WO | WO 93/09722 | 5/1993 |
| WO | WO 96/40368 | 12/1996 |
| WO | WO 97/10753 | 3/1997 |
| WO | WO 98/24378 | 6/1998 |
| WO | 9837814 A1 | 9/1998 |
| WO | WO 99/13936 | 3/1999 |
| WO | WO 99/60924 | 12/1999 |
| WO | WO 00/07530 | 2/2000 |
| WO | 0062680 A1 | 10/2000 |
| WO | WO 01/78809 A1 | 10/2001 |
| WO | WO 2004/012586 A2 | 2/2004 |
| WO | WO 2006/058434 A1 | 6/2006 |
| WO | 2008140117 A1 | 11/2008 |
| WO | WO 2008/134457 A1 | 11/2008 |
| WO | WO 2009/004777 A1 | 1/2009 |

OTHER PUBLICATIONS

Abstract only of WO 2005/028001.
Abstract only of WO 2006/124634.
Abstract of WO 99/19008 A1.
International Search Report dated Oct. 19, 2010.
International Search Report dated Oct. 26, 2010.
International Search Report dated Dec. 7, 2010 together with an English language abstract.
U.S. Office Action dated Aug. 16, 2012 issued in U.S. Appl. No. 12/884,845.
U.S. Office Action dated Aug. 27, 2012 issued in U.S. Appl. No. 12/757,210.

(56) References Cited

OTHER PUBLICATIONS

U.S. Office Action dated Aug. 31, 2012 issued in U.S. Appl. No. 12/871,172.
U.S. Non-Final Office Action dated May 21, 2013 issued in corresponding U.S. Appl. No. 12/757,210.
U.S. Final Office Action dated Jan. 18, 2013 issued in corresponding U.S. Appl. No. 12/871,172.
U.S. Final Office Action dated Feb. 4, 2013 issued in corresponding U.S. Appl. No. 12/757,210.
U.S. Final Office Action dated Feb. 7, 2013 issued in corresponding U.S. Appl. No. 12/884,845.
U.S. Non-Final Office Action dated Feb. 6, 2013 issued in corresponding U.S. Appl. No. 12/884,629.
Extended Supplementary European Search Report dated Feb. 5, 2013 issued in corresponding Application No. / Patent No. 10818721.2-1526 / 2481444 PCT/JP2010065851.
Extended Supplementary European Search Report dated Apr. 29, 2013 issued in Application No./Patent No. 10818652.9-1660 / 2481336 PCT/JP2010064674.
Extended Supplementary European Search Report dated Apr. 26, 2013 issued in Application No./Patent No. 10818781.6-1506 / 2481355 PCT/JP2010063321.
U.S. Final Office Action dated Oct. 1, 2013 issued in corresponding U.S. Appl. No. 12/757,210.
U.S. Final Office Action dated Dec. 23, 2013 issued in related U.S. Appl. No. 12/884,629.

* cited by examiner

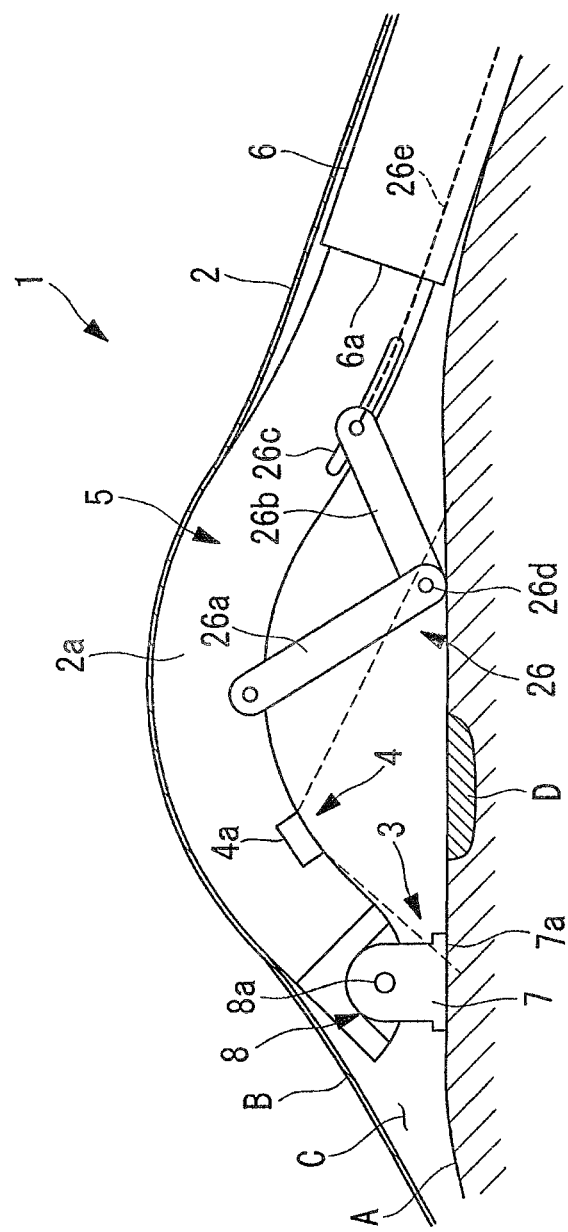

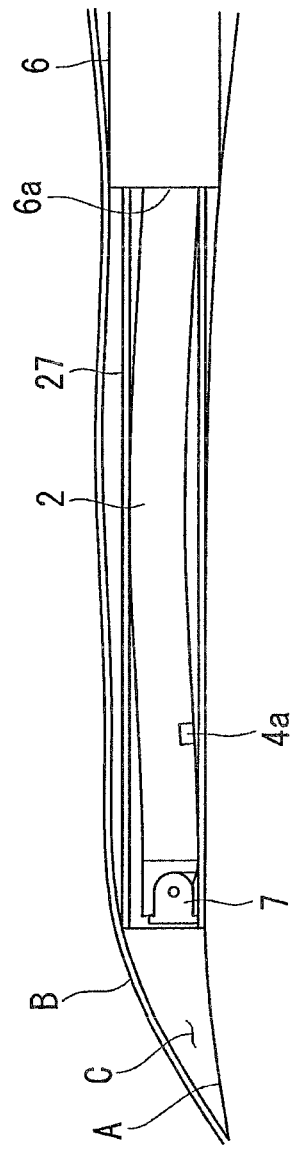
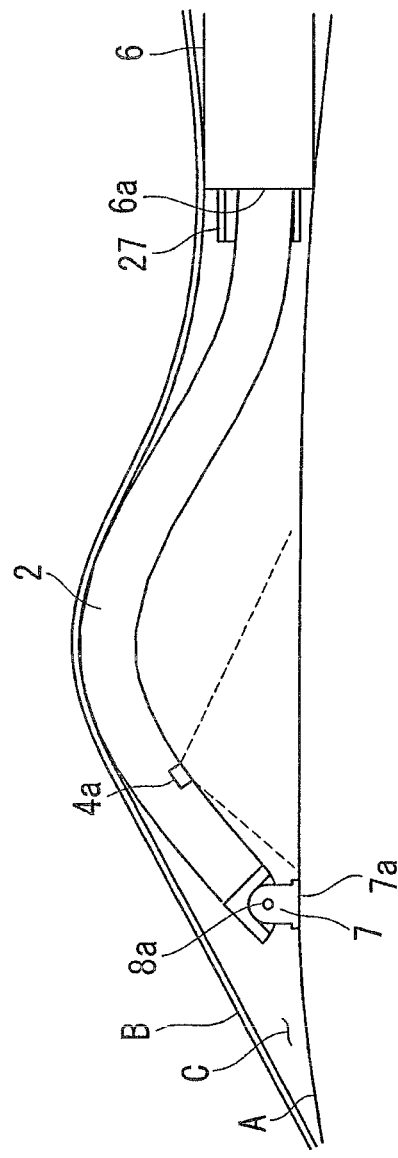

ENDOSCOPY METHOD AND ENDOSCOPE

CROSS REFERENCE TO RELATED APPLICATIONS

This application claims the benefit of U.S. Provisional Application No. 61/244,586, filed Sep. 22, 2009, which is hereby incorporated by reference herein in its entirety.

This application claims the priority under 35 U.S.C. §119 to Japanese Patent Application No. 2009-048460, filed Mar. 2, 2009, and Japanese Patent Application No. 2009-285073, filed Dec. 16, 2009, all of which are hereby incorporated by reference herein in their entirety.

BACKGROUND OF THE INVENTION

1. Field of the Invention

The present invention relates to endoscopy methods and endoscopes.

2. Description of Related Art

There have hitherto been known techniques for temporarily immobilizing the heart by pressing a bar onto the surface of the heart and performing suction in order to stably perform an operation on the heart while suppressing the effect of pulsation (e.g. see PCT International Publication No. WO 97/10753). Since the heart is temporarily immobilized, it becomes possible to attain a stable field of view and to perform an operation stably.

Furthermore, there are known techniques for inserting a flexible endoscope into the pericardial cavity between the heart and the pericardium and performing a procedure (e.g., see U.S. Patent Application Publication No. 2004/0064138).

However, according to the techniques of PCT International Publication No. WO 97/10753, since the heart is temporarily immobilized by securing the surface of the heart to a stationary object in the vicinity, such as an operating table or a rib, there is a disadvantage that a considerable burden is imposed on the patient.

Also, there is a problem with the techniques of U.S. Patent Application Publication No. 2004/0064138 in that, due to the effect of the pulsing heart, the distal end of an endoscope moves uncontrollably in the pericardial cavity, so that it is not possible to attain a stable field of view.

BRIEF SUMMARY OF THE INVENTION

The present invention has been made in view of the situation described above, and it is an object thereof to provide an endoscopy method and an endoscope with which it is possible to attain a stable field of view without having to stop pulsation or the like of the heart or other tissues.

An endoscopy method according to a first aspect of the present invention includes an inserting step of inserting an inserted portion of an endoscope into a body; a securing step of securing a distal-end portion of the inserted portion to tissue inside the body; and an observation-distance adjusting step of adjusting the distance between an observation window of the endoscope and the tissue or adjacent tissue adjacent to the tissue by freeing the inserted portion from the tissue or the adjacent tissue.

In the first aspect, in the insertion step, the inserted portion may be inserted into a gap between tissues, and a space forming step of forming an observation space for the endoscope by widening the gap between tissues may be further included.

In the first aspect, the observation-distance adjusting step may be a step of inflating a balloon between the inserted portion and the tissue or the adjacent tissue.

In the first aspect, the securing step may be a step of securing the inserted portion to the tissue at positions on either side, along a lengthwise direction, of a curving portion provided at the inserted portion, and the observation-distance adjusting step may be a step of curving the curving portion.

In the first aspect, the inserting step may be a step of inserting the inserted portion, which is pretrained into a shape curved at a predetermined curvature, in such a state that the inserted portion is extended to have a curvature smaller than the predetermined curvature, and the observation-distance adjusting step may be a step of releasing the inserted portion from the extended state to the predetermined curvature.

In the first aspect, the observation-distance adjusting step may be a step of pressing an elastic member in a lengthwise direction from a proximal-end of the inserted portion, the elastic member being disposed on a side face of the inserted portion along the lengthwise direction and fixed at a distal end of the inserted portion, thereby projecting the elastic member in a radial direction.

In the first aspect, the observation-distance adjusting step may be a step of moving one end of a plurality of link members in a lengthwise direction of the inserted portion, the plurality of link members being coupled so as to pivot with each other, thereby moving a joint portion in a radial direction.

In the first aspect, the securing step may be a step of securing the inserted portion to the tissue by using a magnetic force, and the observation-distance adjusting step may be a step of adjusting the magnetic force to adjust a magnetic repelling force between the magnetic force and another magnetic force generated from the adjacent tissue.

In the first aspect, the securing step may be a step of securing the inserted portion to the tissue by using a fluid jet, and the observation-distance adjusting step may be a step of adjusting the flow velocity of the fluid jet.

In the first aspect, the inserting step may be a step of inserting the inserted portion from under the xiphoid process into the gap between the heart and the pericardium. In this case, the securing step may be a step of securing the distal-end portion to the heart or the pericardium, and the observation-distance adjusting step may be a step of widening the gap between the heart and the pericardium by freeing from the heart the distal-end portion secured to the heart or the pericardium.

In the first aspect, the inserted portion may be operated under X-ray radiography.

In the first aspect, the inserting step may be a step of inserting the inserted portion between organs adhering to each other.

In the first aspect, the inserting step may be a step of inserting the inserted portion between the lungs, the stomach, the gallbladder, the pancreas, the spleen, the intestines, the kidneys, the urinary bladder, the uterus, the peritoneum, the pleura, or the thoracic diaphragm, between brain tissues, or between skeletal muscles.

An endoscope according to a second aspect of the present invention includes a long, thin inserted portion that is inserted into the body of a patient; securing means for securing the inserted portion to tissue inside the body, the securing means being provided at least at a distal-end portion of the inserted portion; an observation optical system that is provided at the inserted portion and that acquires an image of the tissue or adjacent tissue adjacent to the tissue; and observation-distance adjusting means for adjusting the distance between the observation optical system and a surface of the tissue or a surface of the adjacent tissue.

According to the second aspect of the present invention, by inserting the inserted portion into the body of a patient and securing at least the distal-end portion of the inserted portion to tissue inside the body with the securing means, regardless of the pulsation or the like of the tissue, it is possible to move the observation optical system provided at the inserted portion in synchronization with the pulsation of the tissue, thereby attaining a stable field of view. Furthermore, in this case, by adjusting the distance between the observation optical system and the tissue surface by the operation of the observation-distance adjusting means, it is possible to observe the tissue surface at a distance appropriate for the observation optical system. That is, according to the second aspect of the present invention, since tissue, such as the heart, is not immobilized to a stationary object in the vicinity, without having to stop the pulsation or the like of the tissue, it is possible to attain a stable field of view while alleviating the burden on the patient.

In the second aspect, the securing means may include an attachment unit that attaches to the tissue by using a negative pressure.

Accordingly, by supplying a negative pressure to the attachment unit so that the attachment unit attaches to the tissue, it is possible to readily secure at least the distal-end portion of the inserted portion to the tissue. Furthermore, by stopping the supply of the negative pressure, it is possible to readily release the inserted portion from the tissue.

In the second aspect, the attachment unit may have an attachment surface for attachment to the tissue such that the angle of the attachment surface relative to the inserted portion is changeable.

When the attachment unit is attached to the tissue and the observation-distance adjusting means is operated, the inserted portion is moved in such a state that it is partially restrained by the attachment unit. Thus, by changing the angle of the attachment surface relative to the inserted portion, it is possible to adjust the distance between the observation optical system and the tissue surface while maintaining stable attachment without applying an undue force to the attachment surface or the inserted portion.

In the second aspect, the attachment unit may include an attachment pad having the attachment surface and a joint that joins the attachment pad with the inserted portion so that the attachment pad is pivotable about an axis perpendicular to a lengthwise axis of the inserted portion.

Accordingly, by pivoting the attachment pad relative to the inserted portion via the joint with the attachment surface of the attachment pad attached to the tissue, the angle of the attachment surface relative to the inserted portion is changed. Thus, it is possible to adjust the distance between the observation optical system and the tissue surface while maintaining stable attachment without applying an undue force to the attachment surface or the inserted portion.

In the second aspect, the joint may be a flexible tubular member that conveys a negative pressure to the attachment pad.

Accordingly, by curving the tubular member with the attachment surface of the attachment pad attached to the tissue by the negative pressure conveyed by the tubular member, it is possible to change the angle of the attachment surface relative to the inserted portion.

In the second aspect, the tubular member may be bellows.

In the second aspect, the attachment unit may have a suction hole provided on a side face of the inserted portion.

Accordingly, by supplying a negative pressure to the suction hole so that the attachment unit attaches to the tissue, it is possible to secure the side face of the inserted portion to the tissue.

In the second aspect, a plurality of the attachment units may be provided at intervals along a lengthwise direction, and the observation optical system may be provided between a pair of the attachment units.

Accordingly, it is possible to secure the inserted portion to the tissue on both sides of the observation optical system, so that it is possible to move the observation optical system in synchronization with the tissue even when the tissue pulses, thereby attaining a stable field of view.

In the second aspect, the securing means may include one or more hook members that are hooked to the tissue.

Accordingly, it is possible to mechanically secure the inserted portion to the tissue by hooking the hook members to the tissue.

In the second aspect, the securing means may include a balloon member that is inflated so as to be engaged with a recess of the tissue.

Accordingly, it is possible to secure the inserted portion to the tissue by inserting the inserted portion into the body with the balloon member deflated and then inflating the balloon member so that the balloon member becomes engaged with the recess of the tissue.

In the second aspect, the securing means may include forceps for holding the tissue.

Accordingly, it is possible to secure the inserted portion to the tissue by holding the tissue with the forceps.

In the second aspect, the observation-distance adjusting means may be implemented by a balloon that is disposed between the tissue or the adjacent tissue and the inserted portion and that is inflated or deflated to adjust the distance between the observation optical system and a surface of the tissue or a surface of the adjacent tissue.

Accordingly, by inserting the inserted portion into the body with the balloon deflated and then inflating the balloon disposed between the tissue and the inserted portion, it is possible to move the inserted portion away from the tissue, thereby adjusting the position of the observation optical system.

In the second aspect, a plurality of the securing means may be provided at intervals along a lengthwise direction of the inserted portion, and the observation-distance adjusting means may be implemented by a curving portion that is disposed between the securing means and that curves the inserted portion.

Accordingly, by securing the inserted portion to the tissue at positions spaced along the lengthwise direction with the plurality of securing means and operating the curving portion to curve the inserted portion between the securing means, it is possible to adjust the distance between the observation optical system provided at the inserted portion and the tissue surface.

In the second aspect, the observation-distance adjusting means may be implemented by training the inserted portion into a curved shape.

Accordingly, by simply releasing the inserted portion inside the body, it is possible to restore the inserted portion to the pretrained shape, whereby the distance between the tissue and the observation optical system becomes a predetermined distance.

In the second aspect, the observation-distance adjusting means may include a guide sheath that accommodates the inserted portion in an extended state such that the inserted portion is projectable and retractable from a distal end of the guide sheath.

Accordingly, by inserting the inserted portion into the body in a state accommodated inside the guide sheath and retracting the guide sheath inside the body so that the inserted portion is projected from the distal end of the guide sheath, the inserted portion is released and restored to the pretrained shape, whereby it is possible to adjust the distance between the observation optical system and the tissue surface to a predetermined distance.

In the second aspect, the observation-distance adjusting means may be implemented by an elastic member that is disposed on a side face of the inserted portion along a lengthwise direction, that is fixed at a distal end of the inserted portion, and that is projected in a radial direction by being pushed in the lengthwise direction from a proximal end of the inserted portion.

Accordingly, after inserting the inserted portion into the body with the elastic member disposed on the side face of the inserted portion along the lengthwise direction, the elastic member is pushed in the lengthwise direction from the proximal end toward the distal end, whereby the elastic member is bent and projected in an outward radial direction, and the tissue is pressed by the projected elastic member, whereby it is possible to adjust the distance between the observation optical system and the tissue surface.

In the second aspect, the elastic member may have a cross-sectional shape extending in a circumferential direction of the inserted portion.

Accordingly, it is possible to reduce the degree of bending when the elastic member is curved by being pressed in the lengthwise direction and to project the elastic member in a desired outward radial direction.

In the second aspect, the elastic member may be formed of a bundle of wires arrayed in the circumferential direction of the inserted portion.

Accordingly, since each wire restrains the direction of deformation of the other wires in the bundle, it is possible to reduce the degree of bending when the wires are curved by being pressed in the lengthwise direction and to project the elastic member in a desired outward radial direction.

In the second aspect, the observation-distance adjusting means may be a link mechanism that includes a plurality of link members coupled so as to pivot with each other and that moves a joint portion in a radial direction when one end thereof is moved in a lengthwise direction of the inserted portion.

Accordingly, by inserting the inserted portion into the body with the joint portion extended and the link mechanism disposed along the inserted portion, and inside the body, moving one end of the link mechanism in the lengthwise direction of the inserted portion to project the joint portion in an outward radial direction, the tissue is pressed by the joint portion, whereby it is possible to adjust the distance between the observation optical system and the tissue surface.

In the second aspect, the inserted portion may have a channel for passing various instruments in accordance with procedures performed on the tissue or the adjacent tissue.

Accordingly, it is possible to perform various procedures on the tissue by using instruments introduced into the body through the channel. In this case, since the inserted portion is secured to the tissue, even when the tissue vibrates, the inserted portion is moved in synchronization with the tissue. Thus, it is possible to perform procedures stably by using the instruments.

In the second aspect, the observation optical system may be provided on a side face of the inserted portion, and the channel may have an exit provided at a circumferential position substantially corresponding to the observation optical system.

In the second aspect, preferably, the channel has an exit provided so that an instrument projected from the exit passes through a field of view of the observation optical system.

Accordingly, it is possible with the observation optical system to view the instrument projected into the body from the exit of the channel, so that it is possible to perform a procedure more accurately while visually checking the operation of the instrument.

According to the present invention, an advantage is afforded in that it is possible to attain a stable field of view without having to stop the pulsation or the like of the heart or other tissues.

BRIEF DESCRIPTION OF THE SEVERAL VIEWS OF THE DRAWINGS

FIG. 16 is a front view showing a modification of the endoscope shown in FIG. 1, in which a link mechanism is provided as observation-distance adjusting means;

FIGS. 17A and 17B are partially cutaway front views showing a modification of the endoscope shown in FIG. 1, in which an inserted portion having a pretrained shape is provided as observation-distance adjusting means;

DETAILED DESCRIPTION OF THE INVENTION

An endoscope 1 according to a first embodiment of the present invention will be described below with reference to the drawings.

Figure 1:
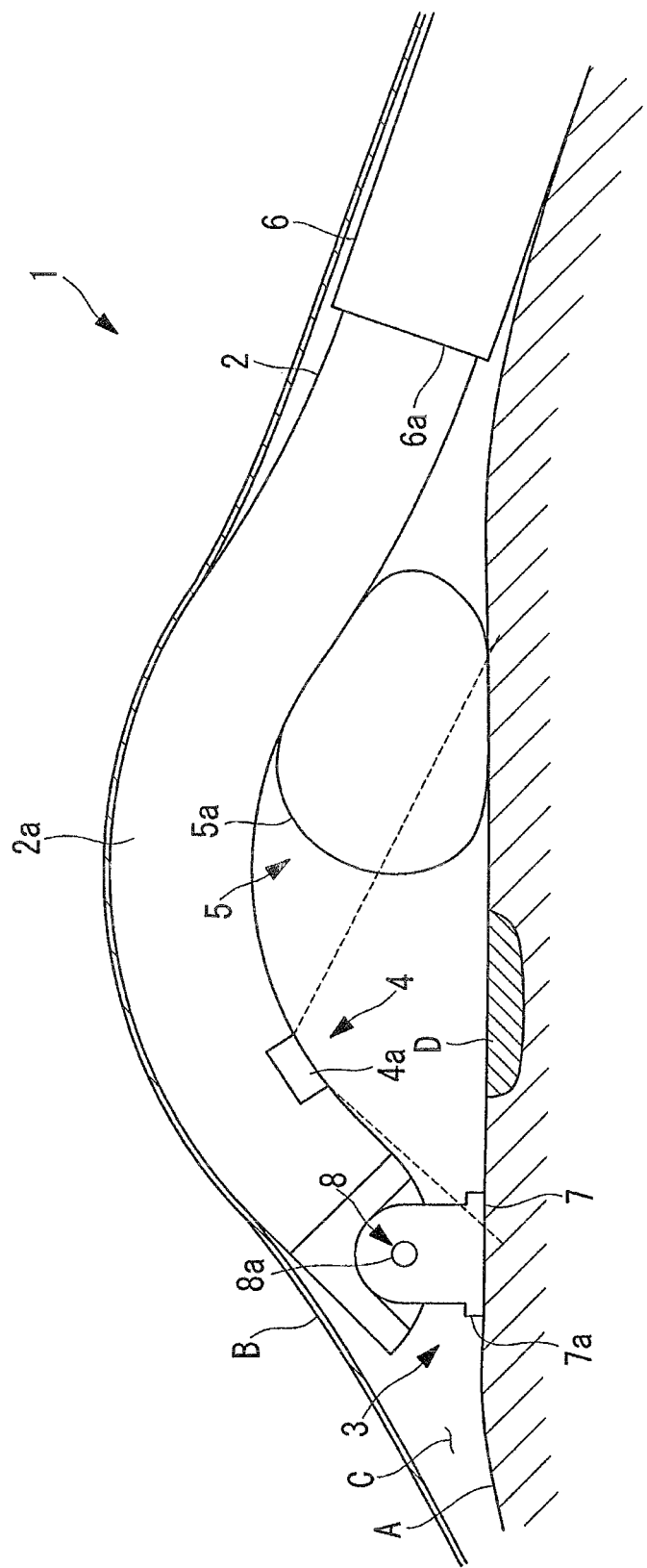
FIG. 1 is a front view of a distal-end portion of an inserted portion of an endoscope according to a first embodiment of the present invention.

As shown in FIG. 1, the endoscope 1 according to this embodiment includes a long, thin, flexible inserted portion 2 that is inserted into a body, securing means 3 that secures the distal end of the inserted portion 2 to tissue (e.g., the heart A) inside the body, an observation optical system 4 that is provided on the side face of the inserted portion 2 and that acquires images in outward radial directions, and observation-distance adjusting means 5 that adjusts the distance between the observation optical system 4 and the surface of the heart A.

FIG. 1 is an illustration showing the state of the distal end of the inserted portion 2 of the endoscope 1 inserted into the pericardial cavity C between the heart A and the pericardium B by a guide sheath 6.

As shown in FIG. 1, the inserted portion 2 has a curving portion 2a at a distal-end portion thereof, which can be curved in order to orient the distal-end face in an arbitrary direction.

The inserted portion 2 has an outer dimension smaller than the inner diameter of the guide sheath 6. When the inserted portion 2 is inserted into the pericardial cavity C, the inserted portion 2 is accommodated inside the guide sheath 6 such that it can be projected and retracted through a distal-end opening 6a of the guide sheath 6.

Figure 2:
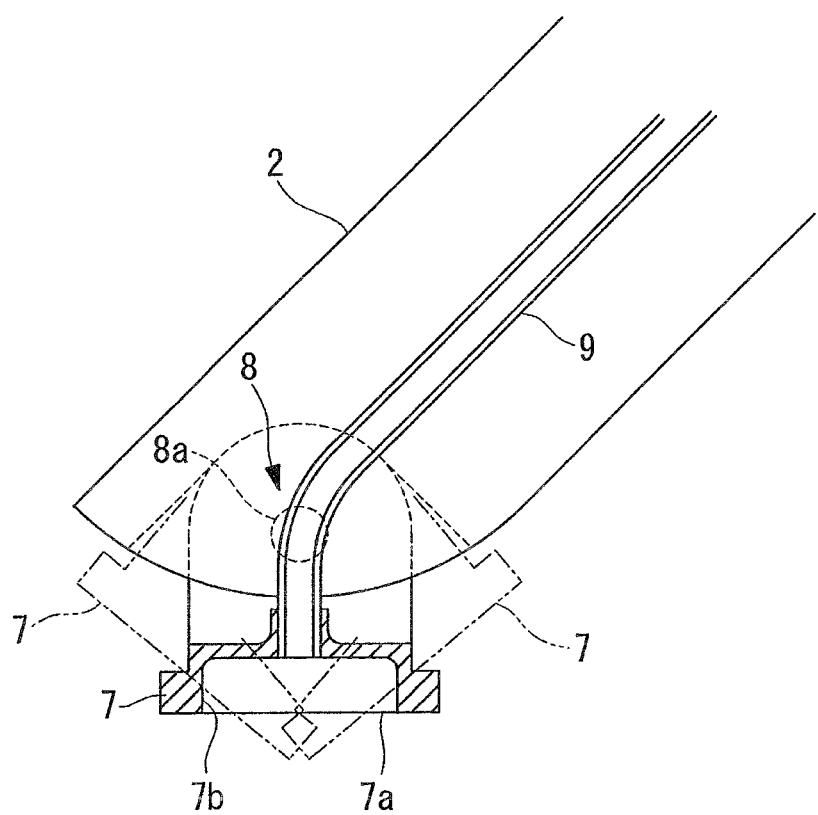
FIG. 2 is a schematic longitudinal sectional view showing, in a further enlarged fashion, the distal end of the inserted portion of the endoscope shown in FIG. 1.

As shown in FIG. 2, the securing means 3 includes an attachment pad 7 provided at the distal end of the inserted portion 2, a joint 8 that joins the attachment pad 7 pivotally with the distal end of the inserted portion 2, and a duct 9 for supplying a negative pressure to an attachment surface 7a of the attachment pad 7. For example, the attachment pad 7 is composed of an elastic material, such as polyurethane rubber or silicone rubber. The attachment pad 7 has a flat attachment surface 7a having a suction hole 7b that can be opened in one direction.

The joint 8 includes a shaft 8a that is disposed along a radial direction of the inserted portion 2, and the joint 8 joins the attachment pad 7 with the inserted portion 2 pivotally about the shaft 8a. Thus, it is possible to change the angle of the attachment surface 7a in one direction with respect to the lengthwise axis of the inserted portion 2. Furthermore, by supplying a negative pressure to the attachment surface 7a of the attachment pad 7 via the duct 9, it is possible to attach the attachment pad 7 to the heart A disposed so as to close the suction hole 7b.

The observation optical system 4 has an observation window 4a provided on the side face of the inserted portion 2 at a position slightly toward the proximal end from the distal end. Inside the inserted portion 2, there are provided an objective lens (not shown) that collects light entering from radially outward of the inserted portion 2 through the observation window 4a and an image capturing element (not shown), such as a CCD, for forming images by using the light collected by the objective lens.

The observation-distance adjusting means 5 includes a balloon 5a disposed on the side face of the inserted portion 2 and a pipe (not shown) for supplying compressed air to the balloon 5a. The balloon 5a is secured at a circumferential position substantially corresponding to the observation window 4a of the inserted portion 2 and is connected to the flue provided inside the inserted portion 2. When the inserted portion 2 is inserted into the body, at which time the inserted portion 2 is accommodated inside the guide sheath 6, the balloon 5a is deflated and is disposed over the circumferential surface of the inserted portion 2. When the inserted portion 2 is projected through the distal-end opening 6a of the guide sheath 6 as shown in FIG. 1, the balloon 5a is inflated by compressed air supplied through the flue.

By inflating the balloon 5a, the surface of the heart A is pressed by the balloon 5a, so that the inserted portion 2 is moved away from the surface of the heart A. This makes it possible to adjust the distance between the observation window 4a provided on the side face of the inserted portion 2 and the surface of the heart A. The observation optical system 4 has a sufficient depth of field to enable focusing within a predetermined distance range from the observation window 4a. Thus, the balloon 5a is configured so that it is possible to adjust the distance between the observation window 4a and the surface of the heart A within a distance range covering the depth of field. The balloon 5a is composed of an elastic material, such as polyurethane rubber or silicone rubber.

The operation of the thus-configured endoscope 1 according to this embodiment will be described below.

Figure 3A:
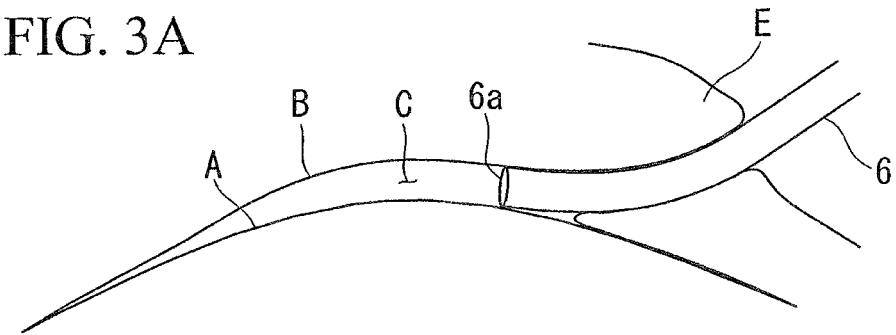
FIGS. 3A to 3D are illustrations for explaining an insertion operation of the endoscope shown in FIG. 1.
Figure 3B:
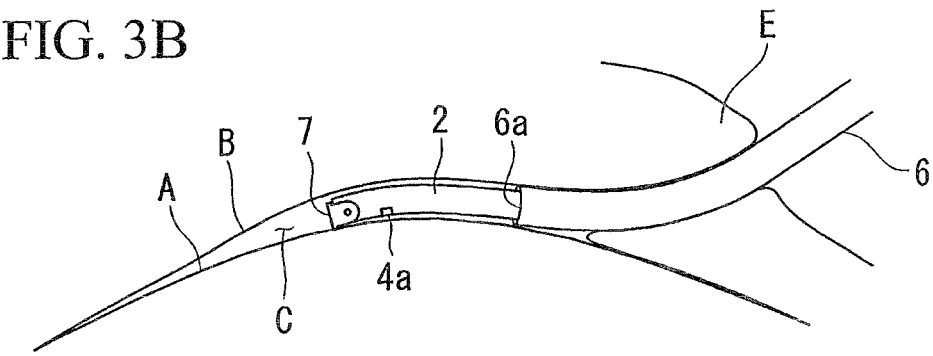

In order to observe tissue inside a body by using the endoscope 1 according to this embodiment, for example, a necrosed region D or the like existing on the outer surface of the heart A, as shown in FIG. 3A, the guide sheath 6 accommodating the inserted portion 2 and the attachment pad 7 is inserted into the pericardial cavity C from the bottom of the xiphoid process E through the pericardium B while observing the guide sheath 6 under x-ray radiography. In this state, as shown in FIG. 3B, the inserted portion 2 of the endoscope 1 inside the guide sheath 6 is pushed out from the distal-end opening 6a of the guide sheath 6.

Figure 3C:
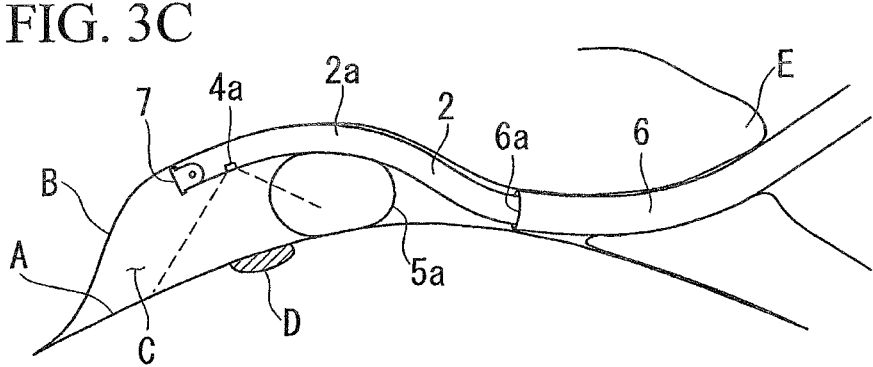

In this state, as shown in FIG. 3C, the balloon 5a disposed between the inserted portion 2 and the surface of the heart A is inflated, whereby the inserted portion 2 is freed from the surface of the heart A. Accordingly, a distance is provided between the observation window 4a provided on the side face of the inserted portion 2 and the surface of the heart A, whereby an appropriate observation distance is formed. Then, the observation optical system 4 is operated to acquire an image of the surface of the heart A, and an affected area existing on the surface of the heart A, such as the necrosed region D, is observed.

Figure 3D:
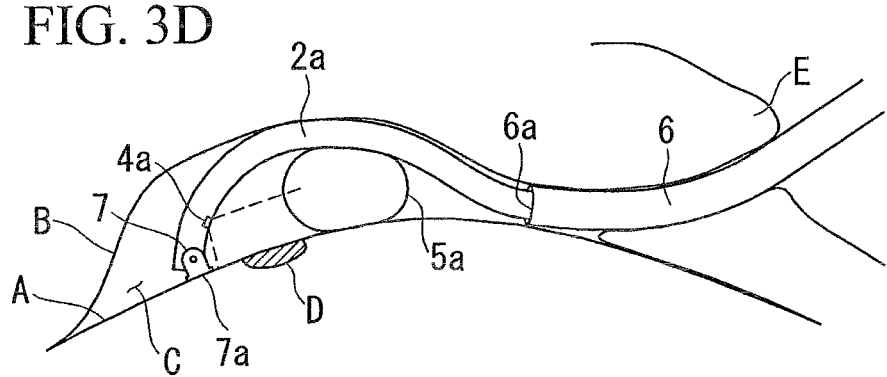

Then, as shown in FIG. 3D, the curving portion 2a provided at the inserted portion 2 is operated so that the attachment surface 7a of the attachment pad 7 provided at the distal end of the inserted portion 2 approaches the surface of the heart A. Then, a negative pressure is supplied to the attachment pad 7 so that the attachment surface 7a is attached to the surface of the heart A. Thus, the inserted portion 2 is secured to the heart A, so that it is possible to move the inserted portion 2 in synchronization with pulsation of the heart A. Accordingly, it becomes possible to acquire substantially still images of an affected area, such as the necrosed region D, regardless of the pulsation of the heart A. That is, an advantage is afforded in that it is possible to perform observation stably without having to stop pulsation of the heart A.

In this case, with the endoscope 1 according to this embodiment, since the attachment pad 7 is pivotally joined with the inserted portion 2 by the joint 8, it is possible to readily change the angle of the inserted portion 2 relative to the attachment pad 7 attached to the surface of the heart A. Thus, application of undue forces to the attachment pad 7 or the inserted portion 2 is prevented, so that it is possible to keep the attachment surface 7a of the attachment pad 7 properly attached to the surface of the heart A.

Figure 4:
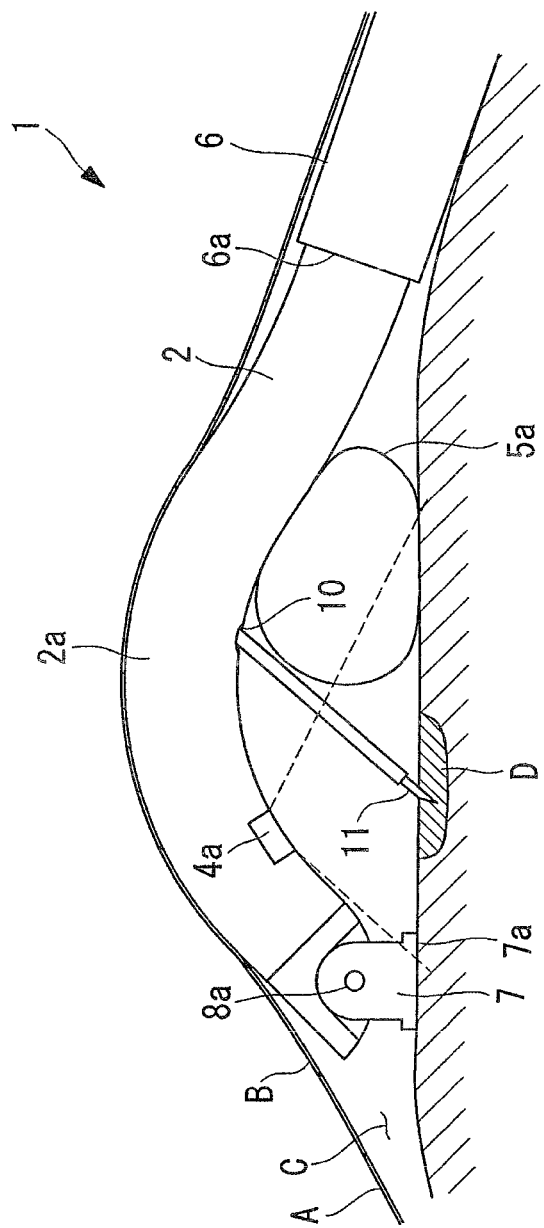
FIG. 4 is a front view showing an example of an instrument that is projected from the exit of a channel provided in the endoscope shown in FIG. 1.

In the endoscope 1 according to this embodiment, as shown in FIG. 4, a channel for guiding an instrument may be provided. The channel is provided from the proximal end of the inserted portion 2 along the lengthwise direction and extends to an exit 10 provided between the balloon 5a and the observation window 4a. Thus, an instrument (e.g., a needle) 11 inserted from the proximal end of the inserted portion 2 is projected from the exit 10, which is provided on the distal-end side of the inserted portion 2 relative to the balloon 5a. The exit 10 is preferably provided at a circumferential position substantially corresponding to the observation window 4a. Furthermore, the exit 10 is preferably provided so that the distal end of the instrument 11 is projected within the field of view of the observation optical system 4. Accordingly, it is possible to manipulate the instrument 11 projected from the exit 10 while viewing it with the observation optical system 4.

In this case, according to this embodiment, the attachment pad 7 is attached to the surface of the heart A to secure the inserted portion 2 to the heart A. Thus, it is possible to immobilize the exit 10 of the channel relative to an affected area, such as the necrosed region D. Accordingly, an advantage is afforded in that it is possible to perform a procedure stably regardless of pulsation of the heart A.

Figure 5:
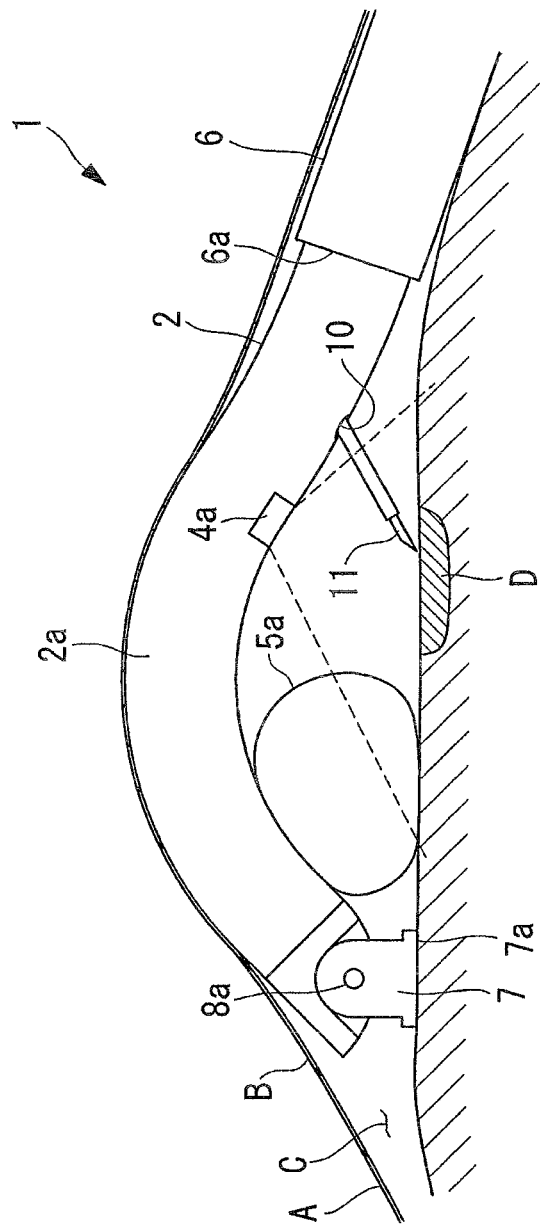
FIG. 5 is a front view showing a modification of the placement of a balloon, an observation window, and the channel of the endoscope shown in FIG. 4.

Although the exit 10 of the channel is provided between the balloon 5a and the observation window 4a in this embodiment, alternatively, as shown in FIG. 5, when the balloon 5a is provided on the distal-end side relative to the observation window 4a, the exit 10 of the channel may be provided on the proximal-end side of the inserted portion 2 relative to the observation window 4a.

Figure 6A:
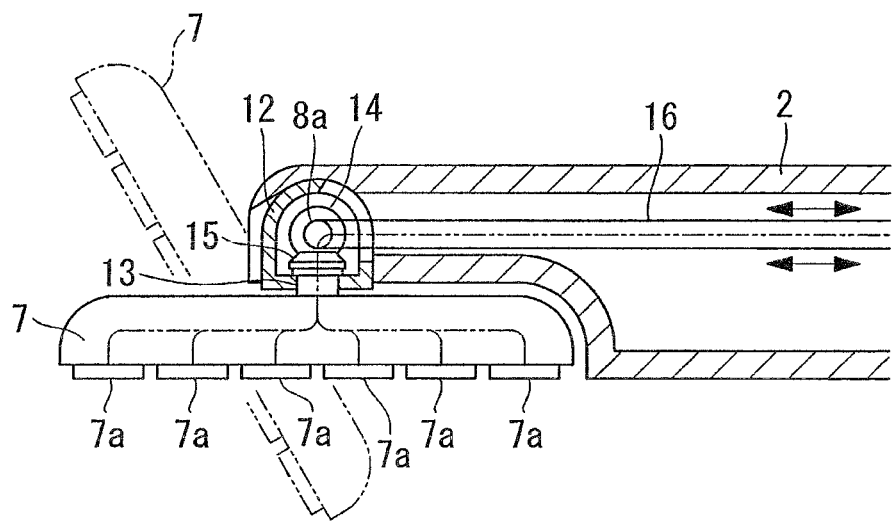
FIG. 6A is a longitudinal sectional view showing a modification of an attachment pad of the endoscope shown in FIG. 1.
Figure 6B:
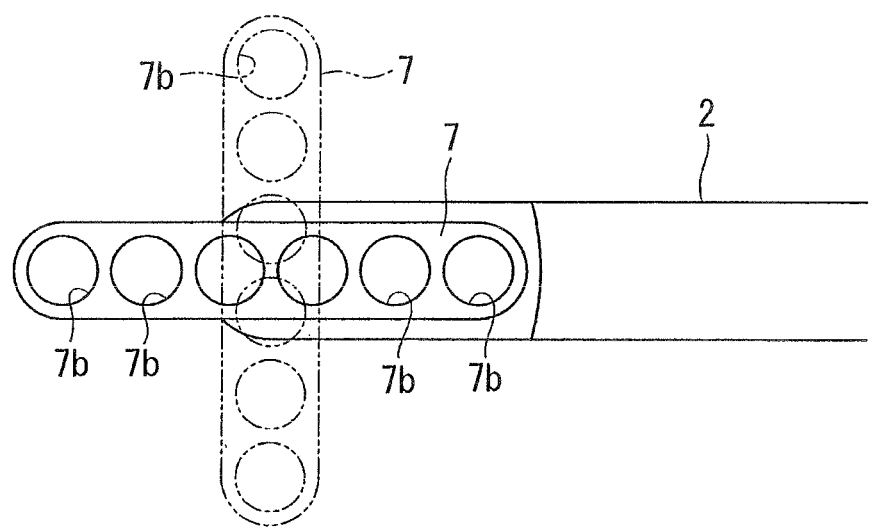
FIG. 6B is an illustration of the modification of the attachment pad of the endoscope shown in FIG. 1, as viewed from the side of an attachment surface.

Furthermore, although an example has been described in which the attachment pad 7 has the single suction hole 7b and is attached so as to pivot only in one direction, alternatively, as shown in FIGS. 6A and 6B, the attachment pad 7 may have a plurality of suction holes 7b and be attached so as to pivot about two mutually perpendicular axes.

More specifically, the attachment pad 7 is attached to a pivot member 12 attached at the distal end of the inserted portion 2 so as to pivot about the shaft 8a disposed perpendicularly to the lengthwise axis such that the attachment pad 7 is pivotable about an axis 13 that is perpendicular to the lengthwise axis of the inserted portion 2 and to the shaft 8a. Thus, by pivoting the pivot member 12 relative to the inserted portion 2 and rotating the attachment pad 7 relative to the pivot member 12, it is possible to pivot the attachment pad 7 about the mutually perpendicular two axes.

The attachment pad 7 is rotatable by a rotary driving mechanism configured of a driving gear 14 provided at the shaft 8a, a driven gear 15 provided at the attachment pad 7 and engaged with the driving gear 14, and a wire 16 wound on the shaft 8a. That is, regardless of the pivot angle of the pivot member 12, by pushing and pulling the wire 16 at the proximal end of the inserted portion 2, the shaft 8a is rotated to rotate the driving gear 14, thereby rotating the driven gear 15 engaged with the driving gear 14, whereby the attachment pad 7 to which the driven gear 15 is fixed can be rotated about the axis 13.

In this case, as indicated by solid lines in FIGS. 6A and 6B, the inserted portion 2 is inserted into the body with the attachment pad 7 oriented along the lengthwise axis of the inserted portion 2, and inside the body, the attachment pad 7 is rotated about the axis 13 so that it is oriented as indicated by a chain line in FIG. 6B. Thus, the inserted portion 2 remains attached to the surface of the heart A against a torsion moment about the lengthwise axis applied to the inserted portion 2. Accordingly, it is possible to support the inserted portion 2 more stably so that the inserted portion 2 is secured relative to the heart A regardless of pulsation of the heart A.

In this case, preferably, negative pressures are supplied independently to the plurality of suction holes 7b provided on the attachment pad 7. That is, since the surface of the tissue of the heart A is not flat, in some cases, it is not possible to simultaneously attach all the suction holes 7b. Even in such cases, by supplying negative pressures independently, the plurality of suction holes 7a can be attached individually.

Figure 7A:
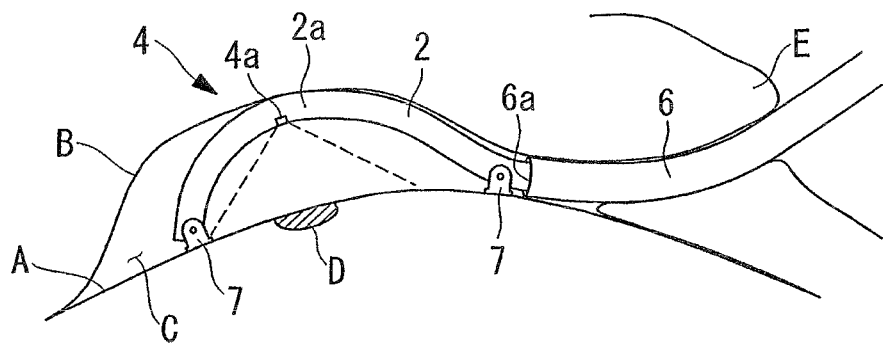
FIG. 7A is a front view for explaining a modification of the endoscope shown in FIG. 1, in which two attachment pads are provided.

Furthermore, although the attachment pad 7 is provided only at the distal end of the inserted portion 2 in this embodiment, alternatively, as shown in FIG. 7A, attachment pads 7 may be provided pivotally at two or more positions at the distal end and a midway position of the inserted portion 2 on either side of the curving portion 2a along the lengthwise direction. Accordingly, by attaching the attachment pads 7 to the surface of the heart A at two or more positions, it is possible to secure the inserted portion 2 to the heart A more reliably. Furthermore, by operating and curving the curving portion 2a with the attachment pads 7 attached at two or more positions on either side of the curving portion 2a, as shown in FIG. 7A, it is possible to configure observation-distance adjusting means for adjusting the distance between the observation window 4a and an affected area, such as the necrosed region D.

Figure 7B:
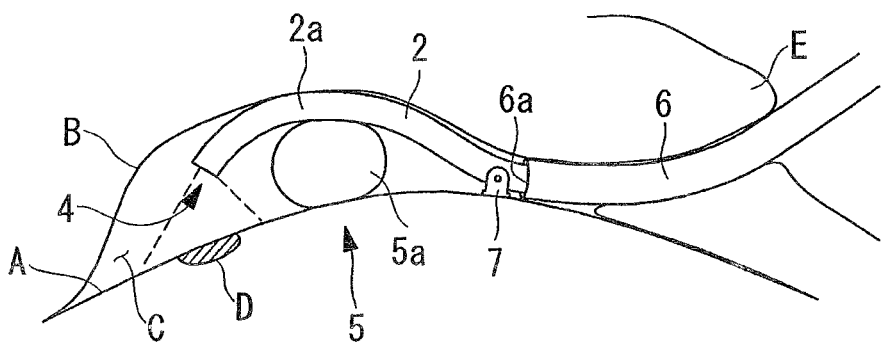
FIG. 7B is a front view for explaining a modification of the endoscope shown in FIG. 1, in which the viewing direction is straight ahead or oblique.

Alternatively, as shown in FIG. 7B, the observation optical system 4 may be provided at the distal end of the endoscope 1 (the viewing direction may be oblique or straight ahead). In this case, the attachment pad 7 should be disposed on the proximal-end side relative to the balloon 5a constituting the observation-distance adjusting means 5. Accordingly, it is possible to curve the distal end of the inserted portion 2 by using the curving portion 2a, thereby readily changing the viewing direction.

Figure 8:
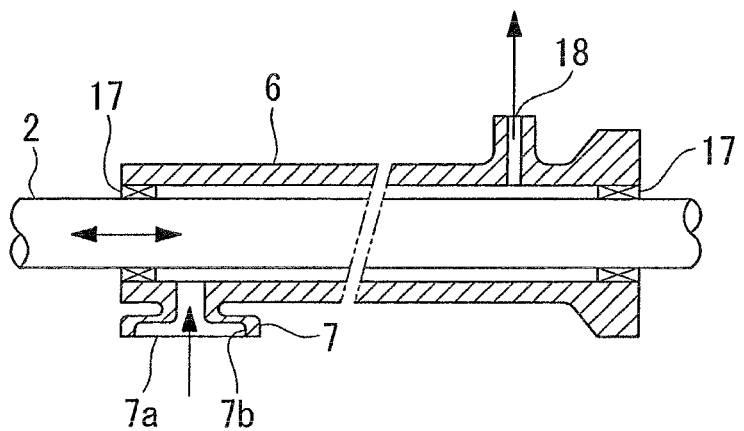
FIG. 8 is a partial longitudinal sectional view for explaining a moving mechanism of one of the attachment pads of the endoscope shown in FIG. 7A.

Alternatively, as shown in FIG. 8, the attachment pad 7 provided at a midway position of the inserted portion 2 may be fixed at the distal end of the guide sheath 6 extending outside the body of the patient. In FIG. 8, the guide sheath 6 is sealed by sealing members 17 at the distal end and the proximal end, forming a cylindrical space with the inserted portion 2, and supports the inserted portion 2 so that the inserted portion 2 is movable along the lengthwise direction. Furthermore, at the proximal end of the guide sheath 6, a suction hole 18 connected to suction means (not shown) is provided at a position outside the body of the patient, and a negative pressure is supplied to the attachment surface 7a of the attachment pad 7 through the cylindrical space between the guide sheath 6 and the inserted portion 2.

Thus, by moving the inserted portion 2 relative to the guide sheath 6 along the lengthwise direction, it is possible to arbitrarily adjust the gap between the attachment pad 7 provided at the distal end of the inserted portion 2 and the attachment pad 7 provided at the distal end of the guide sheath 6. Accordingly, it is possible to adjust the gap in accordance with the size of the tissue to be attached, such as the heart A, thereby achieving an appropriately attached state.

Alternatively, instead of the attachment pad 7 provided at the midway position of the inserted portion 2, a suction hole 7b may be provided on the side face of the inserted portion 2.

Figure 9A:
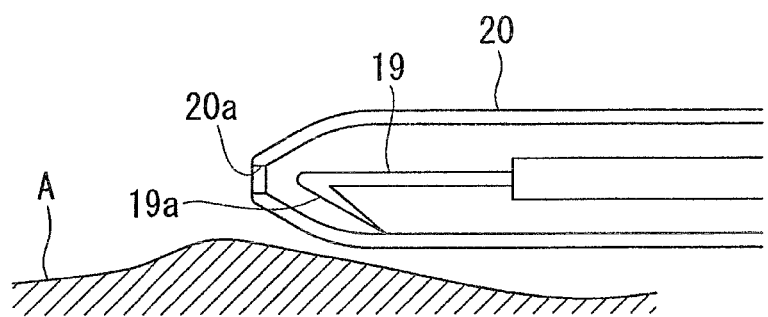
FIGS. 9A to 9C are longitudinal sectional views for explaining an operation of a modification of the endoscope shown in FIG. 1, in which a hook member is provided as securing means.
Figure 9B:
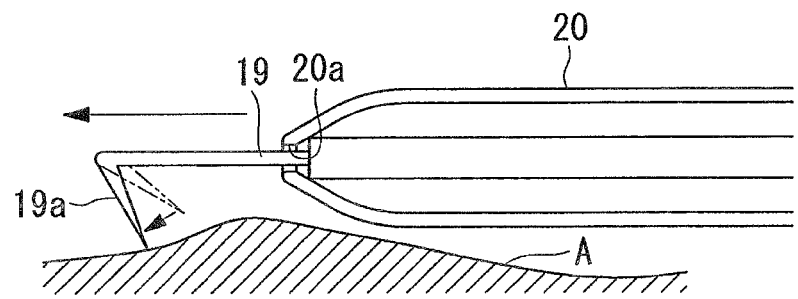
Figure 9C:
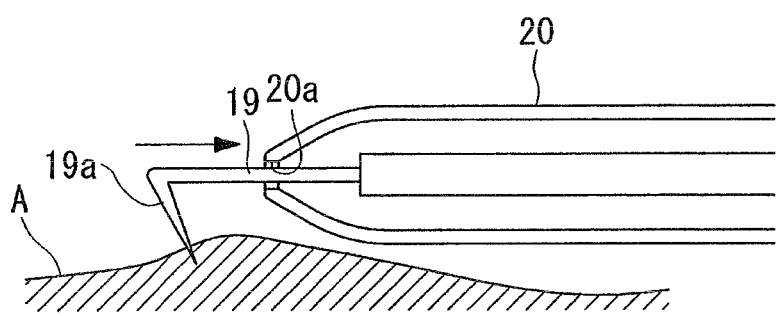

Furthermore, although the embodiment described above is an example provided with the attachment pad 7 pivotally joined by the joint 8 having the shaft 8a, alternatively, as shown in FIGS. 9A to 9C, a hook member 19 that can be hooked to the heart A may be employed as the securing means 3. In the example shown in FIGS. 9A to 9C, for example, the hook member 19 accommodated inside a cylindrical case member 20 is inserted into the body through a forceps channel (not shown) provided along the lengthwise direction of the inserted portion 2.

That is, inside the body, the hook member 19 folded and accommodated in the cylindrical case member 20 as shown in FIG. 9A is projected through a distal-end opening 20a of the cylindrical case member 20, whereby, as shown in FIG. 9B, a hook 19a at the distal end is opened so that the hook 19a readily hooks, and as shown in FIG. 9C, by slightly retracting the hook member 19, it is possible to hook the hook member 19 to tissue, such as the heart A. Accordingly, without supplying power, such as a negative pressure, it is possible to secure the distal end of the inserted portion 2 to tissue, such as the heart A. The number of hook members 19 is not limited to one, and a plurality of hook members 19 may be projected and hooked.

Figure 10:
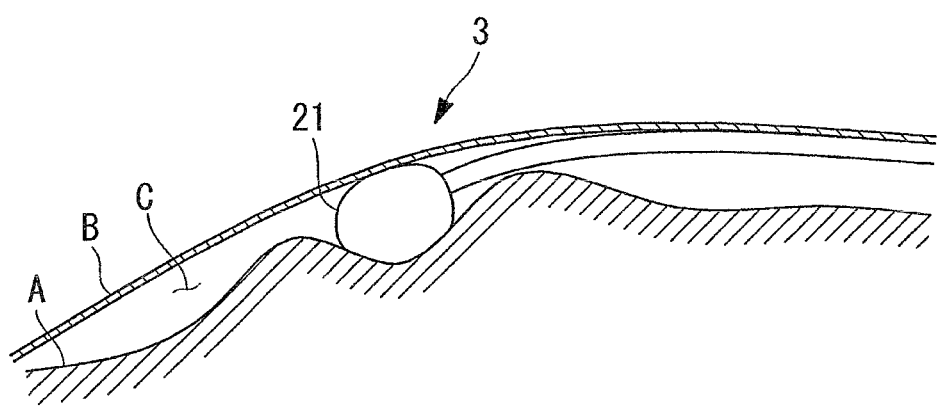
FIG. 10 is an illustration for explaining a modification of the endoscope shown in FIG. 1, in which a balloon member is provided as securing means.

Alternatively, in a case where the tissue has projections and recesses, for example, in a case where it is possible to exploit projections and recesses on the surface of the heart A, a balloon member 21 may be employed as the securing means 3, as shown in FIG. 10. That is, similarly to the case described above, by projecting the balloon member 21 from the distal end of the inserted portion 2 via the forceps channel and inflating the balloon member 21 in the proximity of a recess on the surface of the heart A in the pericardial cavity C, it is possible to secure the inserted portion 2 held between the pericardium B and the surface of the heart A.

Figure 11:
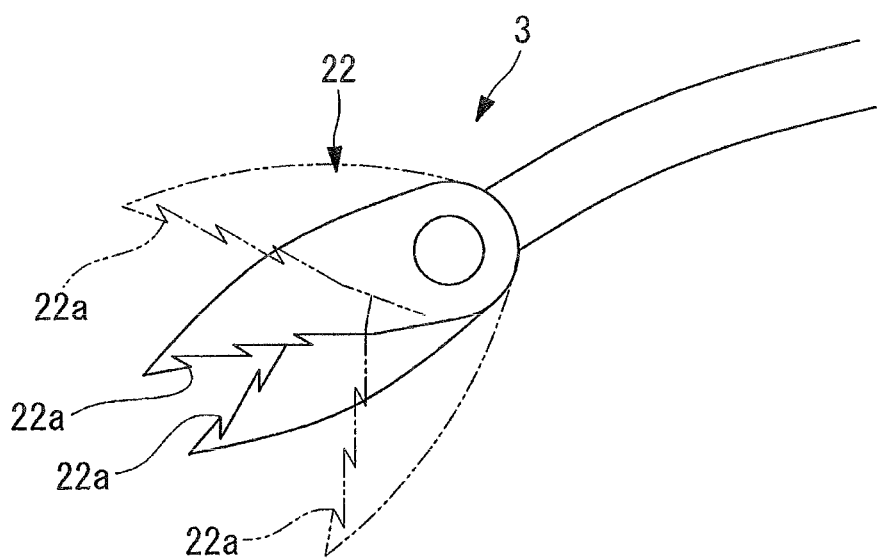
FIG. 11 is an illustration for explaining a modification of the endoscope shown in FIG. 1, in which forceps are provided as securing means.

Instead of the balloon member 21, forceps 22 may be used as the securing means 3, as shown in FIG. 11. That is, by similarly projecting the forceps 22 from the distal end of the inserted portion 2 through the forceps channel and manipulating the forceps 22 to hold the surface of the heart A, it is possible to secure the inserted portion 2 to the surface of the heart A. The forceps 22 preferably have, at their holding regions, a plurality of projections 22a that can be engaged with tissue.

Figure 12:
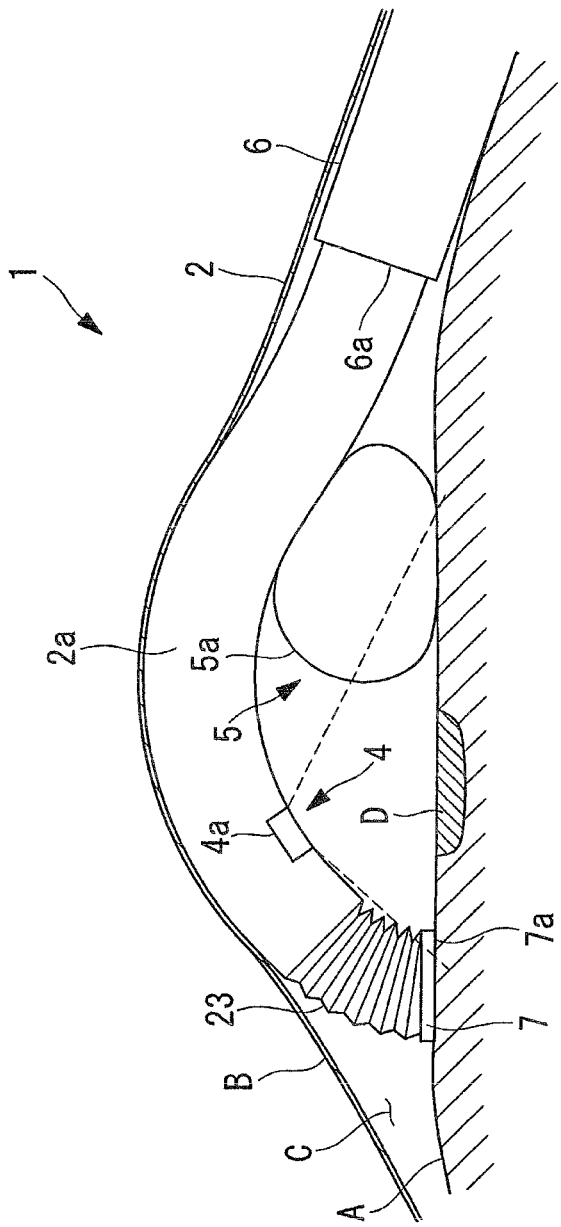
FIG. 12 is a front view for explaining a modification of the endoscope shown in FIG. 1, in which bellows are used as a joint that joints an attachment pad with the inserted portion.

Furthermore, although the shaft 8a disposed along a radial direction of the inserted portion 2 is provided as the joint 8 that pivotally joins the attachment pad 7 at the distal end of the inserted portion 2 in this embodiment, alternatively, as shown in FIG. 12, the attachment pad 7 may be joined at the distal end of the inserted portion 2 by a tubular cylindrical member, such as bellows. Accordingly, by deforming the bellows 23, it is possible to arbitrarily change the angle of the attachment pad 7 relative to the inserted portion 2, and it is also possible to seal the space connected to the attachment pad 7 by the bellows 23 so that a negative pressure supplied to the attachment pad 7 is maintained.

Figure 13A:
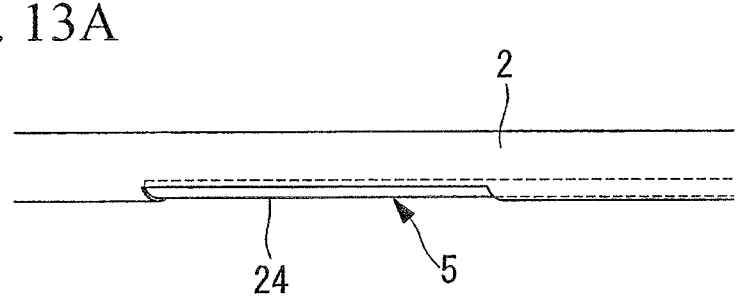
FIGS. 13A and 13B are partial perspective views for explaining a modification of the endoscope shown in FIG. 1, in which a strip-shaped elastic member is provided as observation-distance adjusting means.

Furthermore, although the balloon 5a is employed as the observation-distance adjusting means 5 in this embodiment, alternatively, as shown in FIGS. 13A and 13B and FIGS. 14A and 14B, a strip-shaped elastic member 24 may be employed. For example, when the inserted portion 2 is inserted into the body, the elastic member 24 has a form extending on the outer surface of the inserted portion 2 along the lengthwise direction, as shown in FIG. 13A. The distal end of the elastic member 24 is fixed to the inserted portion 2, and the proximal end thereof is projected from the proximal end of the inserted portion 2 so that it can be pushed and pulled by an operator.

Figure 13B:
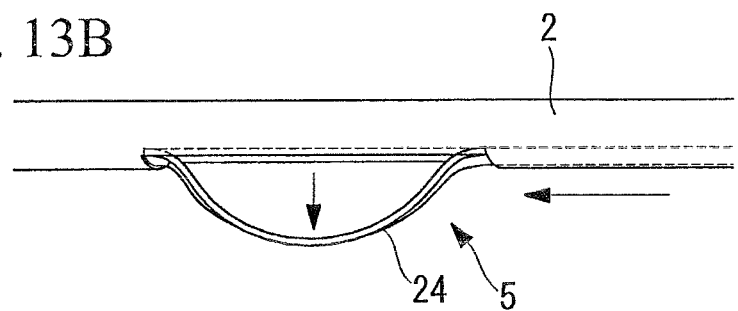

With the inserted portion 2 inserted into the body, when an operator pushes the proximal end of the elastic member 24 toward the distal end, the elastic member 24 curves and projects outward in a radial direction from the inserted portion 2, as shown in FIG. 13B. Thus, it is possible to push the surface of the heart A by the projected elastic member 24, and by adjusting the amount of projection, similarly to the case of the balloon 5a in the embodiment described above, it is possible to adjust the distance between the observation window 4a and the surface of the heart A.

Figure 14A:
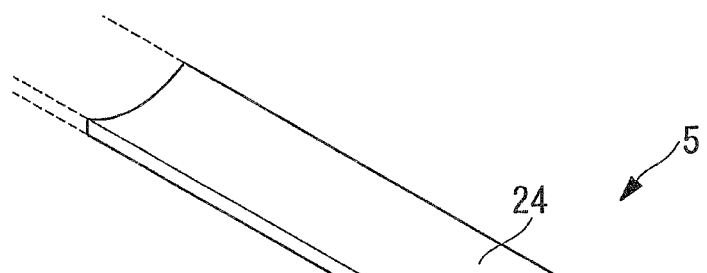
FIGS. 14A and 14B are perspective views for explaining an operation of the elastic member shown in FIGS. 13A and 13B.
Figure 14B:
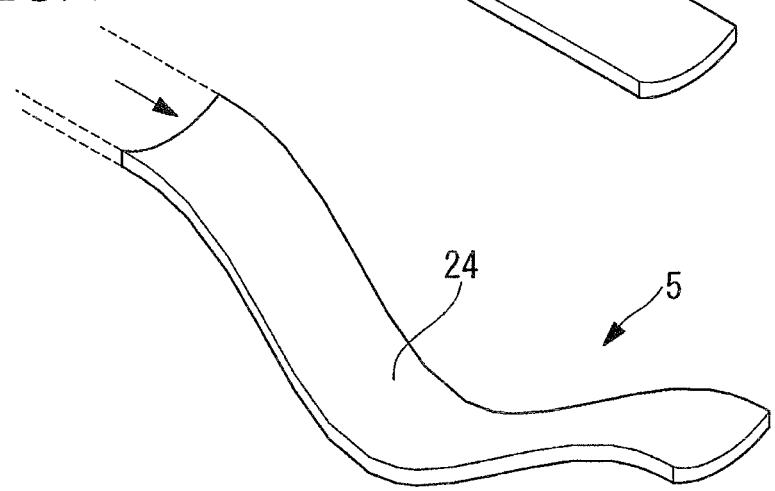

As shown in FIGS. 14A and 14B, the strip-shaped elastic member 24 has a wide shape extending over a predetermined range along the circumferential direction of the inserted portion 2, so that it is possible to stabilize the direction of projection in a radial direction.

Figure 15A:
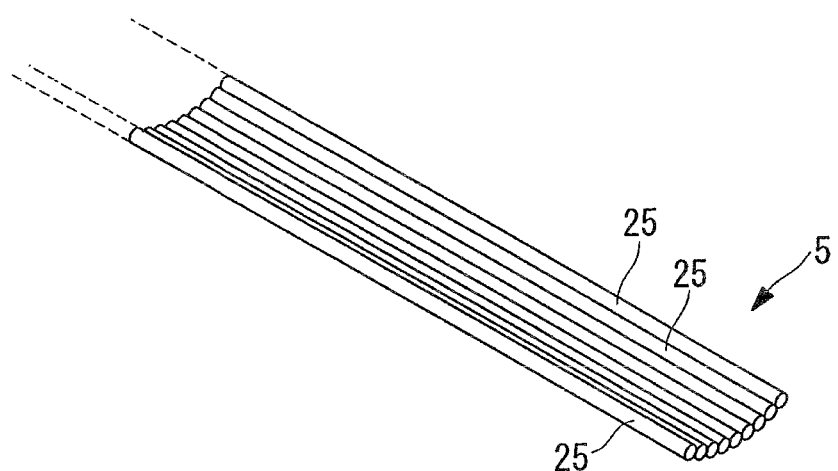
FIGS. 15A and 15B are perspective views showing a bundle of wires that serves as the elastic member shown in FIGS. 14A and 14B.
Figure 15B:
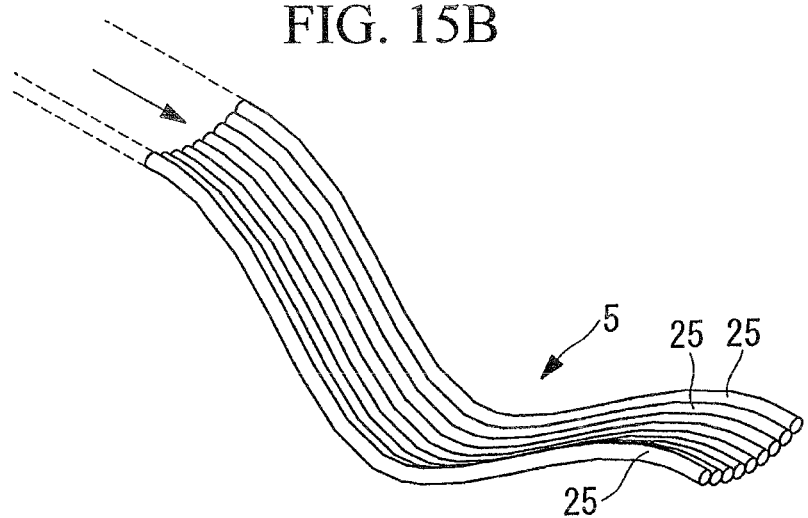

Instead of the strip-shaped elastic member 24, as shown in FIGS. 15A and 15B, a plurality of wires 25 may be bundled such that they are arrayed along the circumferential direction of the inserted portion 2.

Accordingly, at the time of insertion into the body, as shown in FIG. 15A, a tension is applied, and after insertion into the body, as shown in FIG. 15B, the wires 25 are pressed toward the distal end and are thereby bent. Thus, it is possible to press the surface of the heart A and thereby adjust the distance between the observation window 4a and the surface of the heart A.

Alternatively, instead of the strip-shaped elastic member 24 or the plurality of wires 25 described above, as shown in FIG. 16, the observation-distance adjusting means 5 may be configured of a link mechanism 26 including a plurality of (two in FIG. 16) links 26a and 26b. In the example shown in FIG. 16, of the two links 26a and 26b pivotally coupled with each other, the distal end of the link 26a at the distal end is pivotally attached to the inserted portion 2, and by moving the proximal end of the link 26b at the proximal end along a guide groove 26c provided on the inserted portion 2, it is possible to project and retract a joint portion 26d between the links 26a and 26b in a radial direction.

For example, the link 26b at the proximal end is moved by an operation at the proximal end of the inserted portion 2 via a wire 26e.

Alternatively, as shown in FIG. 17B, the distal-end portion of the inserted portion 2 may be trained in advance into a predetermined curved shape, and at the time of insertion into the body, as shown in FIG. 17A, the inserted portion 2 may be accommodated in a guide sheath 27 that is capable of shaping the inserted portion 2 in an extended form. Accordingly, after the inserted portion 2 is inserted into the pericardial cavity C in the state accommodated in the guide sheath 27 as shown in FIG. 17A, by withdrawing the guide sheath 27 toward the proximal end as shown in FIG. 17B, the inserted portion 2 is released and is restored to the pretrained form. Thus, it is possible to readily adjust the distance between the observation window 4a and the surface of the heart A to a preset distance.

Furthermore, the inserted portion 2 may be provided with a plurality of magnets attached with spaces along the lengthwise direction thereof. Accordingly, even when the inserted portion 2 is inserted into the body of the patient, it is possible to identify the positions of the magnets by a magnetic sensor provided outside the body and to visualize the form of the inserted portion 2 in an image.

Furthermore, although the balloon 5a is disposed so as to project in one direction outside the circumference of the inserted portion 2 when the balloon 5a is used as the observation-distance adjusting means 5, alternatively, the balloon 5a may be inflated in all directions. Alternatively, the balloon 5a that can be inflated in all directions may be restrained by using a spool or the like so that it inflates only in one direction.

Furthermore, although the pericardial cavity C between the heart A and the pericardium B is described as an example of a region inside the body that is observed with the endoscope 1 in this embodiment, the observed region is not limited to the pericardial cavity C, and application to other arbitrary tissues is possible.

Next, an endoscope 30 according to a second embodiment of the present invention will be described below with reference to the drawings.

In the description of the endoscope 30 according to this embodiment, parts that are configured the same as those of the endoscope 1 according to the first embodiment described above will be designated by the same reference signs, and descriptions thereof will be omitted.

Figure 18:
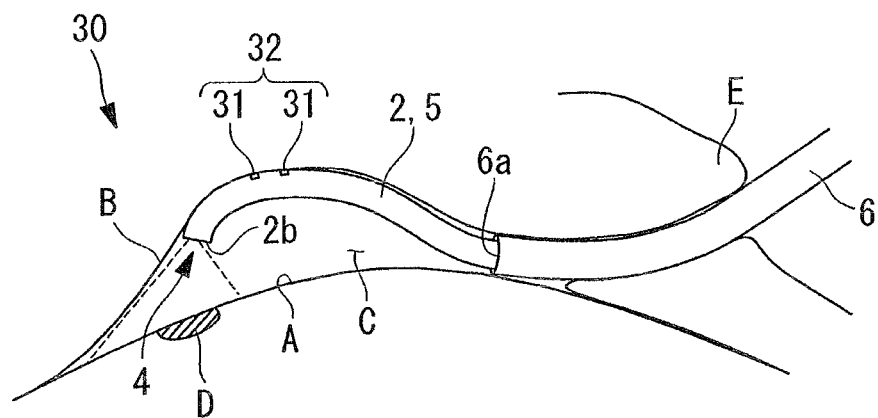
FIG. 18 is a front view of a distal-end portion of an inserted portion of an endoscope according to a second embodiment of the present invention.
Figure 19:
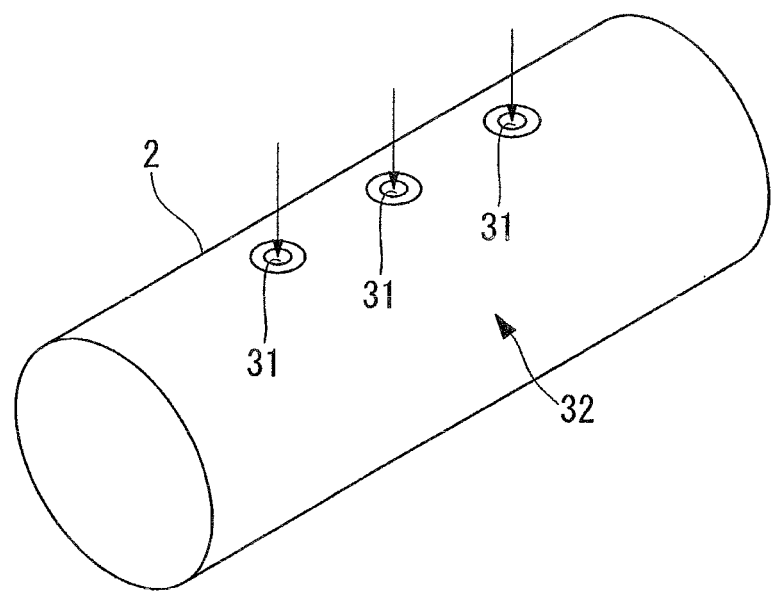
FIG. 19 is a partial perspective view of the inserted portion shown in FIG. 18, showing securing means implemented by suction holes provided at the inserted portion.

As shown in FIGS. 18 and 19, the endoscope 30 according to this embodiment includes securing means 32 having suction holes 31 that are attached to the pericardium B instead of the securing means 3 having the attachment pad 7 that is attached to the surface of the heart A. As shown in FIG. 19, the suction holes 31 constituting the securing means 32 are provided on the side face of the inserted portion 2, and serve to attach the side face of the inserted portion 2 to the pericardium B by a negative pressure supplied via a duct (not shown).

Preferably, multiple suction holes 31 are provided, and the suction holes 31 are provided at intervals along the lengthwise direction of the inserted portion 2 and independently enable attachment with negative pressures. Accordingly, it is possible to switch the suction holes 31 used for attachment with negative pressures and thereby adjust the position where the inserted portion 2 is attached to the pericardium B.

Furthermore, in this embodiment, an inserted portion 2 that itself is trained so as to curve when it is projected from the guide sheath 6, as shown in FIG. 18, is employed as the observation-distance adjusting means 5.

In the endoscope 30 according to this embodiment, the observation optical system 4 that acquires an image at the front is provided at a distal-end face 2b of the inserted portion 2. Furthermore, a forceps channel (not shown) is formed to have an opening at the distal-end face 2b of the inserted portion 2 so that it is possible to project and retract an instrument for manipulating an affected area on the surface of the heart A.

With the thus-configured endoscope 30 according to this embodiment, the inserted portion 2 is curved by projecting the inserted portion 2 of the endoscope 30 from inside the guide sheath 6 into the pericardial cavity C with the distal end of the guide sheath 6 inserted into the pericardial cavity C. Then, the inserted portion 2 is rotated about the lengthwise axis thereof, whereby the inserted portion 2 trained to curve widens the gap between the pericardium B and the surface of the heart A. That is, an observation space is provided in the pericardial cavity C between the pericardium B and the surface of the heart A. Accordingly, it is possible to direct the distal-end face 2b of the inserted portion 2 whose side face is attached to the pericardium B by the securing means 32 toward the surface of the heart A at a location separated from the surface of the heart A.

Compared with the pulsing heart A, the pericardium B can be considered as effectively stationary, and the inserted portion 2 attached to the pericardium B is held by the pericardium B so as not to be displaced considerably regardless of pulsation of the heart A. As a result, by the operation of the observation optical system 4 of the endoscope 30, it is possible to acquire sharp images over a relatively wide range on the surface of the pulsing heart A. That is, a doctor can endoscopically observe the surface of the heart A as if the doctor cut open the chest of the patient by a thoracotomy operation and cut the pericardium B to expose the surface of the heart A. This facilitates observation of a necrosed region of the heart A and a procedure on an affected area.

Although the securing means 32 having the one or more suction holes 31 formed on the side face of the inserted portion 2 is employed for securing the inserted portion 2 to the pericardium B in this embodiment, alternatively, securing means having a single suction hole 31 may be employed. Alternatively, securing means may be employed in which negative pressures are supplied simultaneously to the plurality of suction holes 31. Furthermore, securing means may be employed in which a plurality of suction holes 31 is provided along the circumferential direction.

Figure 20:
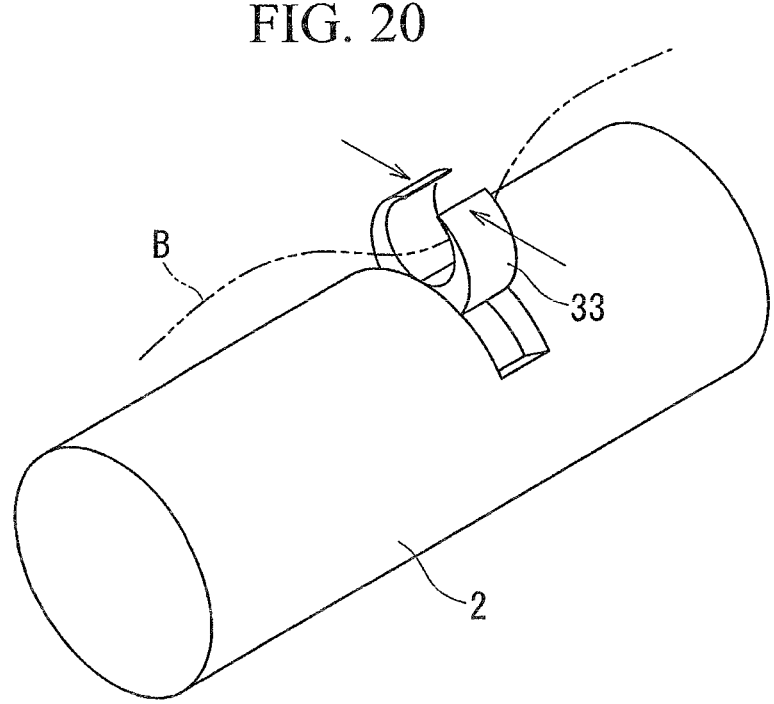
FIG. 20 is a partial perspective view of an inserted portion, showing a modification of the securing means shown in FIG. 19.
Figure 21:
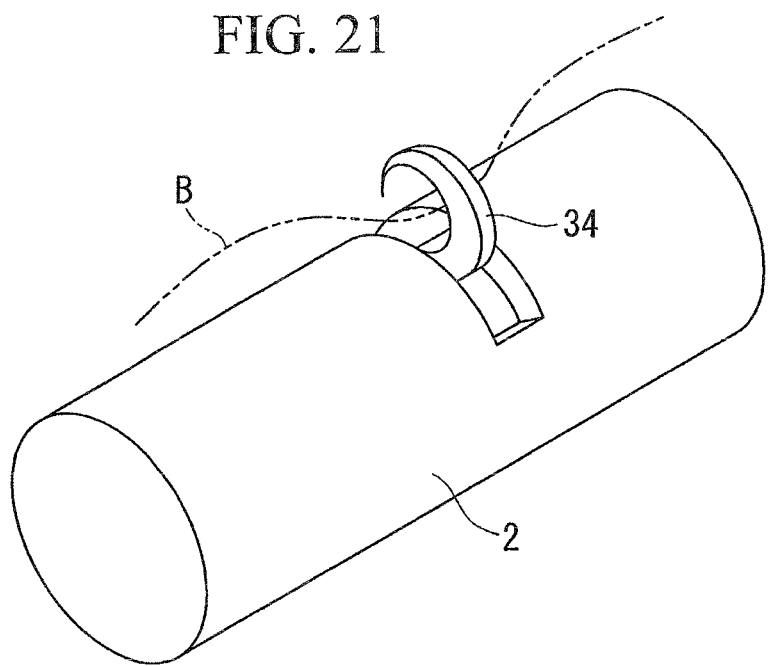
FIG. 21 is a partial perspective view of an inserted portion, showing another modification of the securing means shown in FIG. 19.

Instead of the securing means 32 having the suction holes 31, as shown in FIG. 20, it is possible to employ securing means 33 that is implemented by a holding part provided projectably and retractably on the side face of the inserted portion 2 and projected from the side face of the inserted portion 2 to hold the pericardium B disposed in proximity to the side face of the inserted portion 2. Alternatively, instead of the securing means 33 implemented by the holding part, as shown in FIG. 21, securing means 34 implemented by a hook that pierces the pericardium B may be employed.

Figure 22:
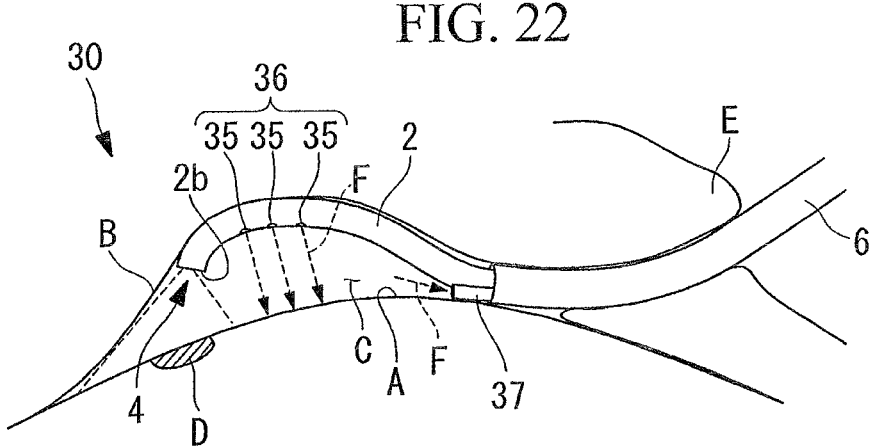
FIG. 22 is a front view of a distal-end portion of an inserted portion, showing a modification including securing means different from that of the endoscope shown in FIG. 18.

Alternatively, instead of the securing means 32 having the suction holes 31, as shown in FIG. 22, it is possible to employ securing means 36 in which a jet 35 for jetting a fluid, for example, air, is provided on the side face of the inserted portion 2, and the inserted portion 2 is pressed against and secured to the pericardium B by the power of the fluid F jetted from the jet 35. In this case, just jetting the fluid F from the jet 35 would fill the inside of the pericardium B with the fluid F. Thus, a discharge duct 37 should be provided to have an opening on the pericardial cavity C so that the supplied fluid F will be discharged outside through the guide sheath 6.

Furthermore, in this case, since the inserted portion 2 is pressed against the pericardium B by the power of the fluid F jetting against the surface of the heart A, preferably, the flow level of the air jetted from the jet 35 is adjusted in synchronization with pulsation of the heart A so that the inserted portion 2 will not be affected by pulsation when the heart A pulses. That is, by adjusting the flow level of the air so that the amount is smaller when the heart A expands and the amount is greater when the heart A contracts, it is possible to minimize the effect of pulsation.

Figure 23:
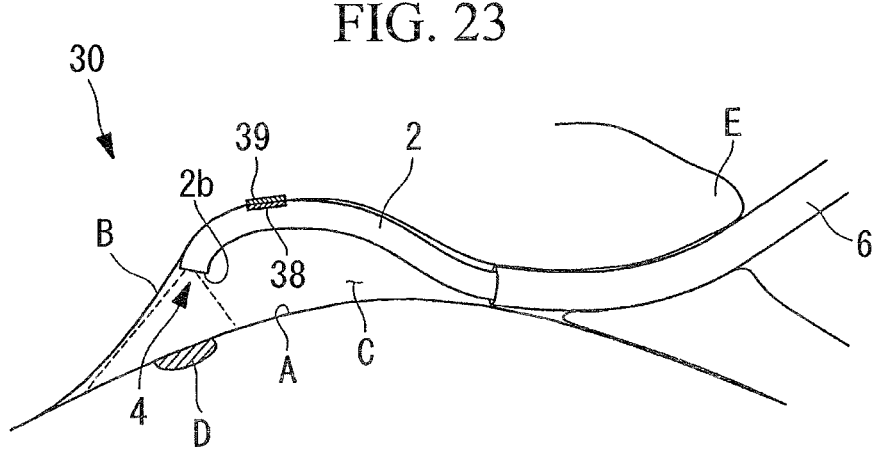
FIG. 23 is a front view of a distal-end portion of an inserted portion, showing a modification including another securing means different from that of the endoscope shown in FIG. 18.
Figure 24:
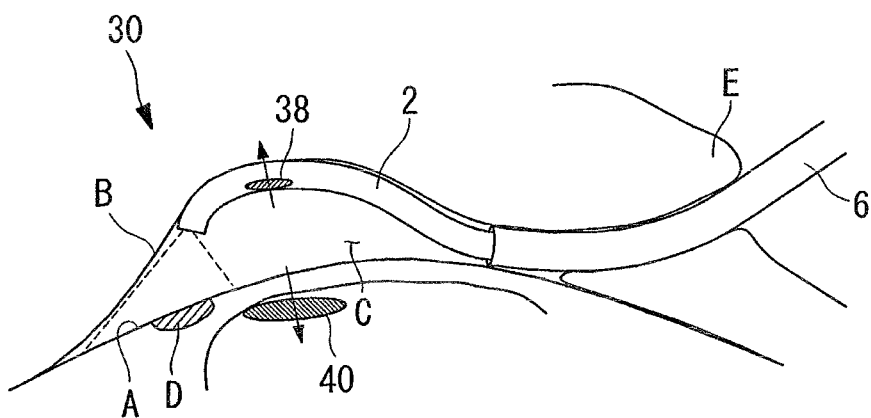
FIG. 24 is a front view of a distal-end portion of an inserted portion, showing a modification including another securing means different from that of the endoscope shown in FIG. 18.

Alternatively, instead of the securing means 32 having the suction holes 31, as shown in FIG. 23 or FIG. 24, securing means implemented by a magnet (magnetic-force generating means) 38 disposed on the side face of the inserted portion 2 may be employed. In the case shown in FIG. 23, a magnet (magnetic-force generating means) 39 is fixed at the pericardium B, so that it is possible to attach the inserted portion 2 to the pericardium B by a magnetic attracting force between the magnet 39 at the pericardium B and the magnet 38 at the inserted portion 2.

On the other hand, in the case shown in FIG. 24, a magnet 40 (magnetic-force generating means) 40 is fixed inside the heart A, so that it is possible to press the inserted portion 2 toward and secure the inserted portion 2 to the pericardium B by a magnetic repelling force between the magnet 40 at the heart A and the magnet 38 at the inserted portion 2.

In this case, by using an electromagnet as at least one of the magnet 40 fixed inside the heart A and the magnet 38 provided at the inserted portion 2 and adjusting the magnetic force generated by the electromagnet, it is possible to adjust the magnetic repelling force. Observation-distance adjusting means may be implemented in this manner.

Figure 25:
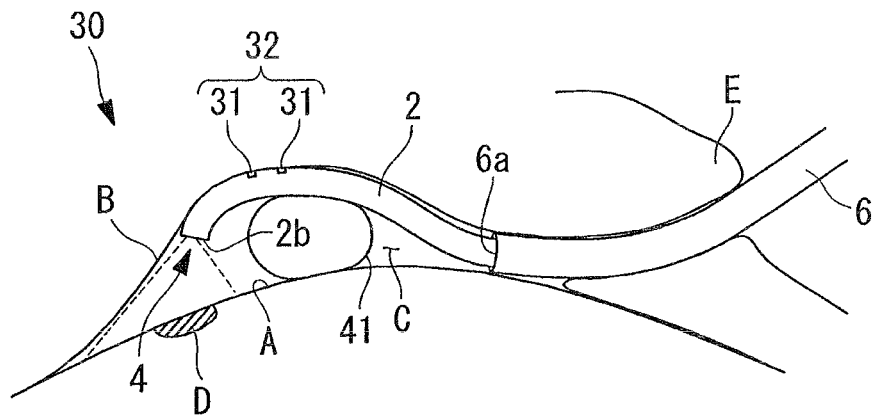
FIG. 25 is a front view of a distal-end portion of an inserted portion, showing a modification including observation-distance adjusting means different from that of the endoscope shown in FIG. 18.

Furthermore, although the inserted portion 2 which itself is trained to curve is employed as the observation-distance adjusting means 5, alternatively, as shown in FIG. 25, a balloon 41 that is disposed between the inserted portion 2 and the surface of the heart A and that is inflated or deflated may be employed. By inflating the balloon 41 with the inserted portion 2 attached to the pericardium B, it is possible to form an observation space in the pericardial cavity C between the pericardium B and the surface of the heart A. Furthermore, it is possible to adjust the observation distance by changing the degree of inflation of the balloon 41. Furthermore, by pressing the balloon 41 against the surface of the heart A, it is possible to alleviate the pulsation of the heart A, thereby further suppressing blurring of images acquired by the observation optical system 4.

Furthermore, the endoscopes 1 and 30 according to the embodiments described above may be modified in the following manners.

First, a plurality of balloons 5a or 41 may be arrayed along the lengthwise direction of the inserted portion 2, which may be capable of being inflated or deflated independently.

Figure 26:
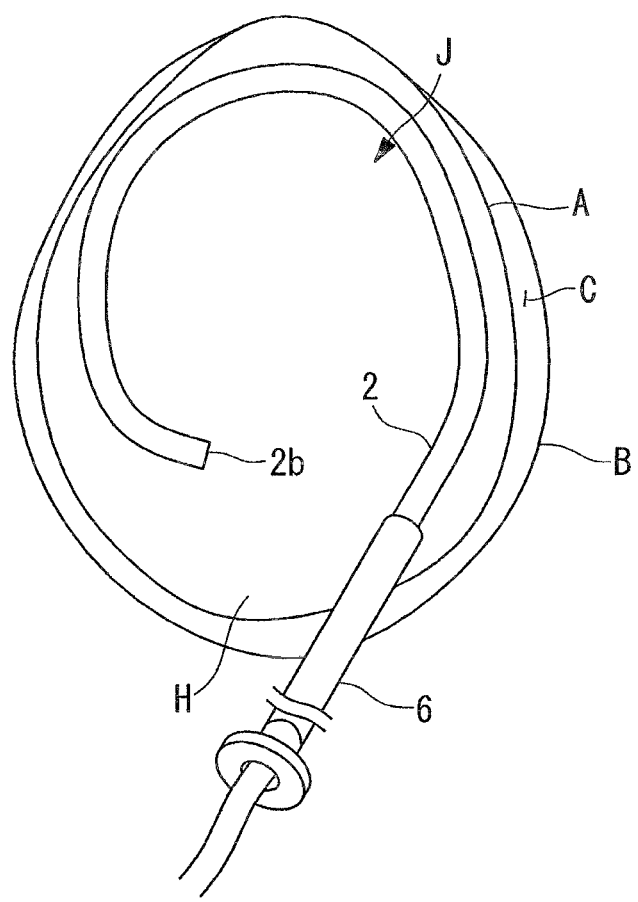
FIG. 26 is a plan view of a distal-end portion of an inserted portion, showing a modification including another observation-distance adjusting means different from that of the endoscope shown in FIG. 18.
Figure 27:
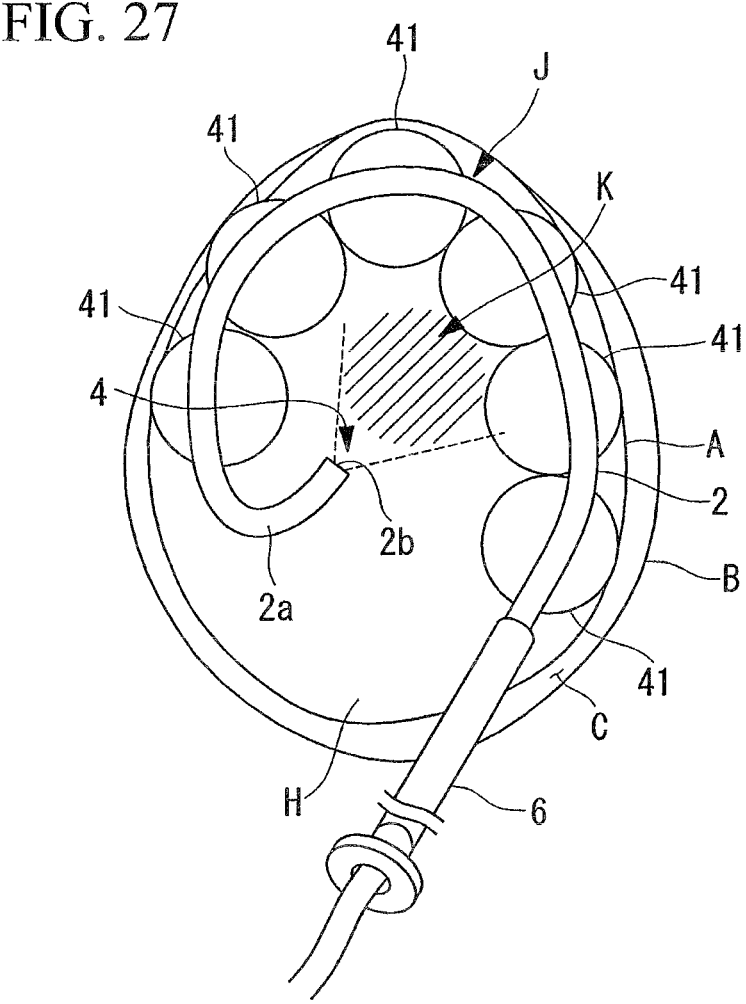
FIG. 27 is a plan view of the distal-end portion of the inserted portion, showing a state where all the balloons constituting the observation-distance adjusting means of the endoscope shown in FIG. 26 are inflated.
Figure 28:
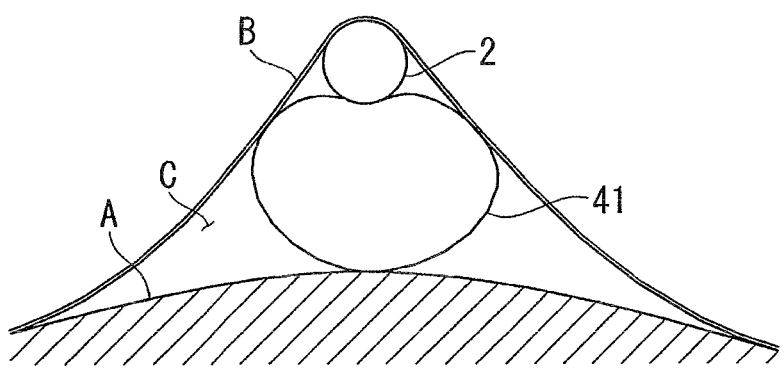
FIG. 28 is a cross-sectional view of the balloons and the inserted portion of the endoscope shown in FIG. 27.

For example, as shown in FIG. 26, from the guide sheath 6 inserted from the bottom of the xiphoid process E through the abdomen into the pericardial cavity C in the proximity of the heart apex H, the inserted portion 2 is inserted into the pericardial cavity C and curved into a substantially U shape at the pericardial turnover region J so that the distal-end face 2b is directed toward the heart apex H. In this state, as shown in FIG. 27, the balloons 41 are inflated, whereby an observation space indicated as a hatched region K is provided in the vicinity of the distal-end face 2b of the inserted portion 2 in the pericardial cavity C between the surface of the heart A and the pericardium B. Furthermore, as shown in FIG. 28, the inserted portion 2 is secured in a state pressed against the pericardium B by the balloons 41.

Furthermore, by curving the curving portion 2a of the inserted portion 2 in this state, a wide field of view for the observation optical system 4 is provided in the space surrounded by the balloons 41 and formed between the pericardium B and the surface of the heart A, so that it is possible to perform detailed observation. Furthermore, by adjusting the amount of inflation of the balloons 41 in synchronization with pulsation timing, it is possible to further stabilize the field of view. That is, by adjusting the amount of inflation of the balloons 41 so that it becomes smaller when the heart A expands and it becomes greater when the heart A contracts, it is possible to maintain the distance between the pericardium B and the surface of the heart A constant, so that the field of view is further stabilized.

Figure 29:
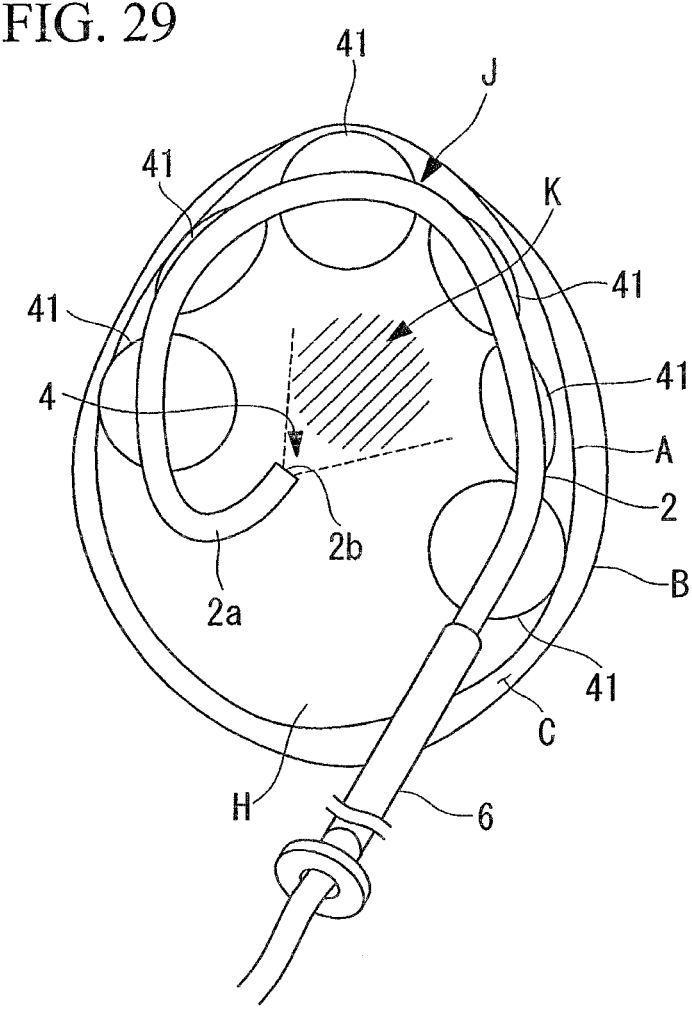
FIG. 29 is a plan view of the distal-end portion of the inserted portion, showing a state where some of the balloons constituting the observation-distance adjusting means of the endoscope shown in FIG. 26 are inflated.

In this case, as shown in FIG. 29, it is possible to ensure only the minimum necessary space by selecting the balloons 41 to be inflated as needed.

Figure 30:
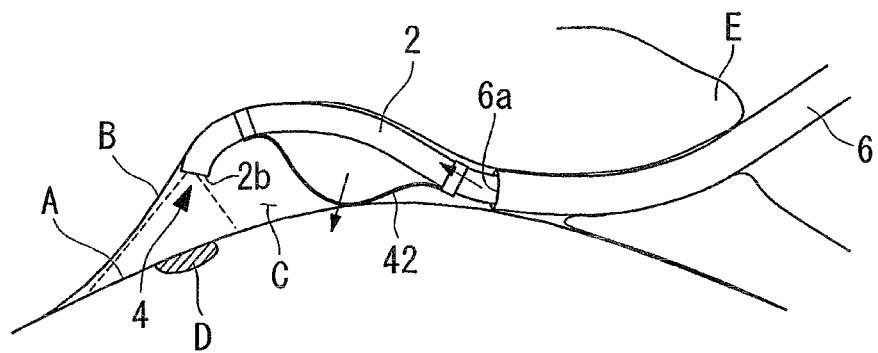
FIG. 30 is a front view of a distal-end portion of an inserted portion, showing a modification including another observation-distance adjusting means different from that of the endoscope shown in FIG. 18.
Figure 31:
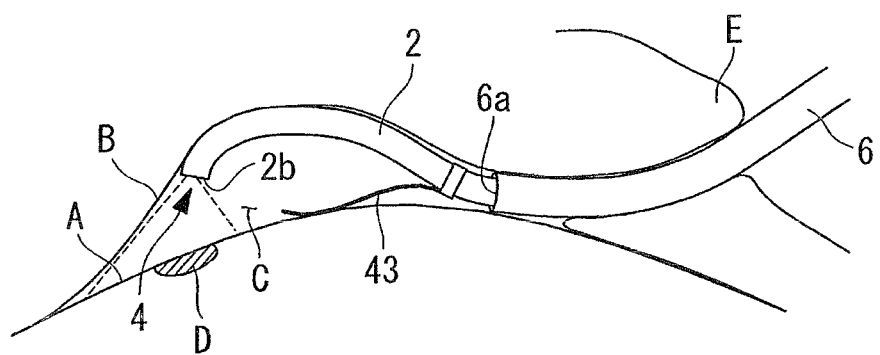
FIG. 31 is a front view of a distal-end portion of an inserted portion, showing a modification including another observation-distance adjusting means different from that of the endoscope shown in FIG. 18.
Figure 32:
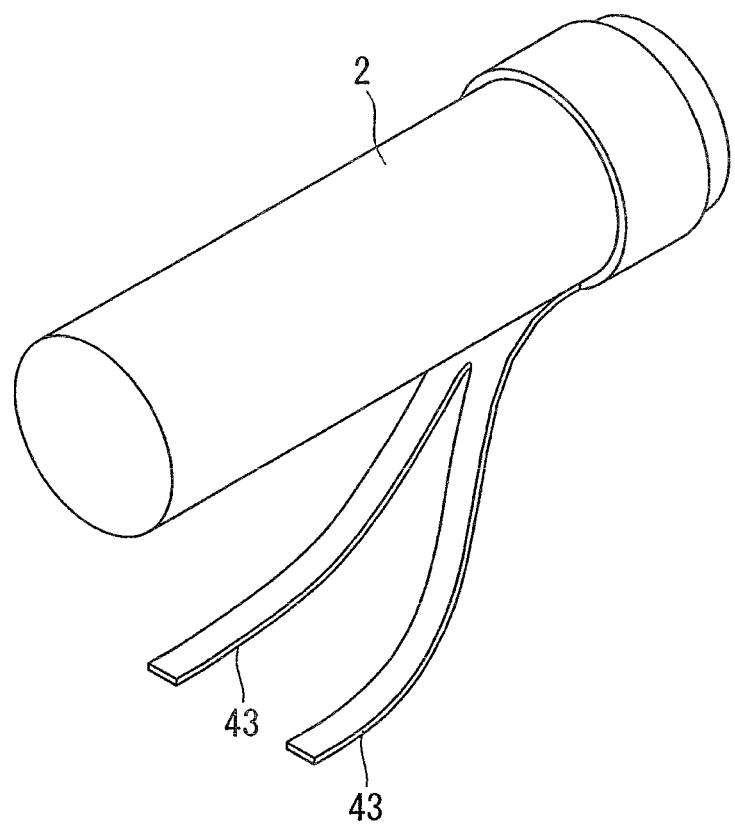
FIG. 32 is a partial perspective view of an inserted portion, showing a modification of the observation-distance adjusting means shown in FIG. 31.

Secondly, instead of the balloons 41, as shown in FIG. 30 or FIG. 31, observation-distance adjusting means may be implemented by a spring 42 or a retention bar 43 that is released and expanded when the inserted portion 2 is projected from the guide sheath 6. Preferably, the retention bar 43 has such a structure that it projects so as to come in contact with the surface of the heart A at two or more positions. Accordingly, it is possible to stabilize the inserted portion 2 so that it is not twisted by pulsation of the heart A.

Figure 33:
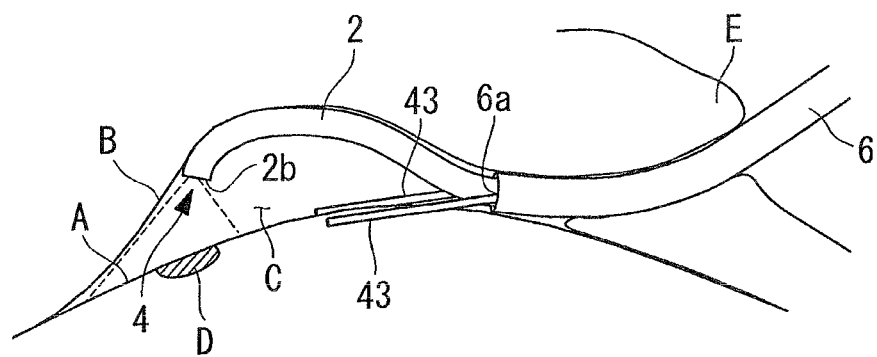
FIG. 33 is a front view of a distal-end portion of an inserted portion, showing a modification including another observation-distance adjusting means different from that of the endoscope shown in FIG. 18.

Alternatively, the retention bar 43 may be projected from the guide sheath 6, as shown in FIG. 33.

Alternatively, a retention bar may be configured of a link mechanism 26 similar to that shown in FIG. 16, and the amount of projection may be adjusted by the link mechanism 26.

Figure 34:
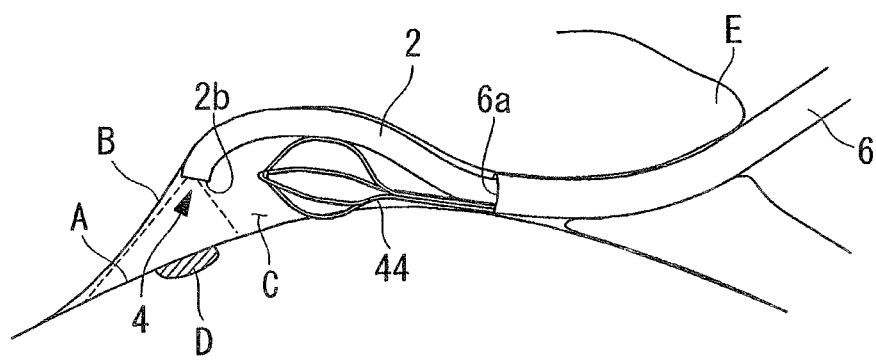
FIG. 34 is a front view of a distal-end portion of an inserted portion, showing a modification including another observation-distance adjusting means different from that of the endoscope shown in FIG. 18.
Figure 35:
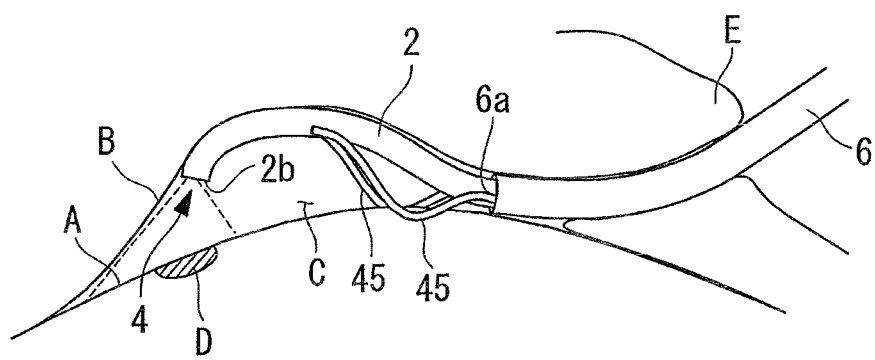
FIG. 35 is a front view of a distal-end portion of an inserted portion, showing a modification including another observation-distance adjusting means different from that of the endoscope shown in FIG. 18.

Alternatively, a space may be provided in the pericardial cavity C between the pericardium B and the surface of the heart A by using a basket 44 formed of wires and configured to expand when the inserted portion 2 is projected from the guide sheath 6, as shown in FIG. 34, or by using tubular members 45 or a wire member trained to curve as shown in FIG. 35.

Figure 36:
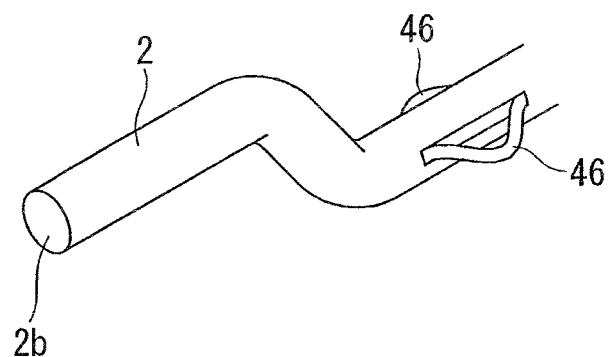
FIG. 36 is a partial perspective view showing an inserted portion of an endoscope, provided with means for stabilizing the inserted portion relative to the pulsation of the heart.

Alternatively, in order to stabilize the inserted portion 2 projected from the guide sheath 6 against pulsation of the heart A, as shown in FIG. 36, a stabilizer may be provided that is formed of wires 46 projecting in radial directions from either side face of the inserted portion 2 and coming into contact with the surface of the heart A.

Figure 37:
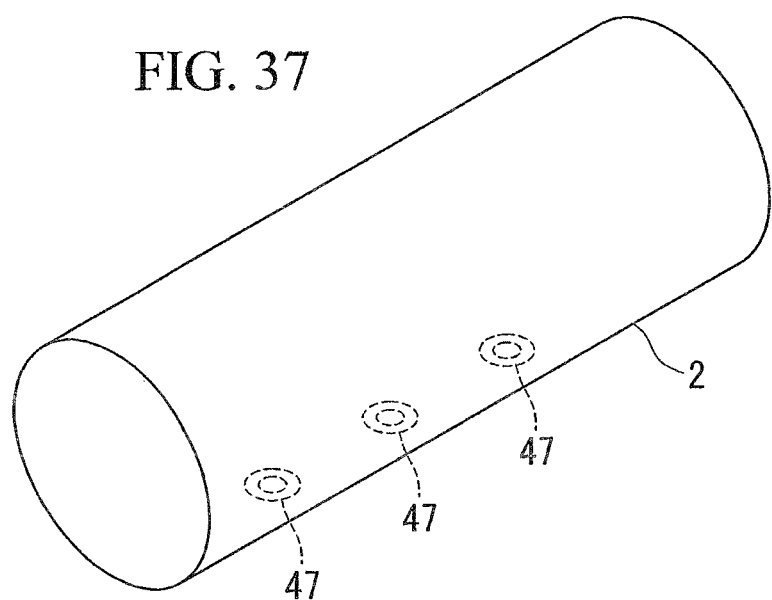
FIG. 37 is a partial perspective view showing an inserted portion of an endoscope, provided with another means for stabilizing the inserted portion relative to the pulsation of the heart.
Figure 38:
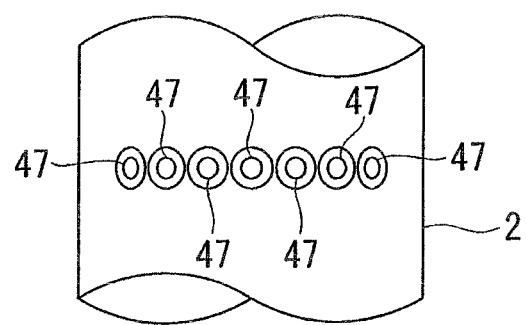
FIG. 38 is a partial perspective view showing an inserted portion of an endoscope, provided with another means for stabilizing the inserted portion relative to the pulsation of the heart.

Alternatively, suction holes 47 may be provided that serve to attach the inserted portion 2 to the surface of the heart A in the proximity of the opening 6a of the guide sheath 6. A plurality of suction holes 47 may be provided with spaces along the lengthwise axis of the inserted portion 2, as shown in FIG. 37, or may be provided along the circumferential direction, as shown in FIG. 38.

Figure 39A:
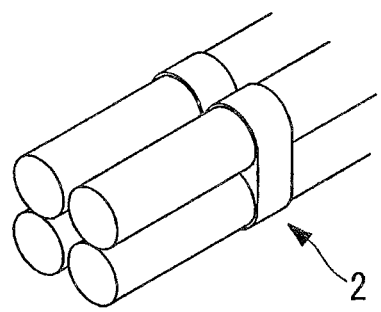
FIG. 39A is a partial perspective view showing an inserted portion of an endoscope, provided with another means for stabilizing the inserted portion relative to the pulsation of the heart, showing a state where the inserted portion is tightly bundled.
Figure 39B:
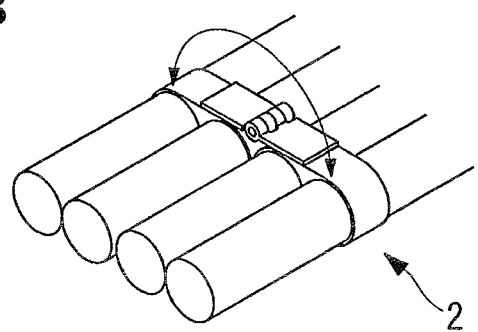
FIG. 39B is a partial perspective view showing an inserted portion of an endoscope, provided with another means for stabilizing the inserted portion relative to the pulsation of the heart, showing a state where the inserted portion is flatly expanded.

Alternatively, as shown in FIGS. 39A and 39B, an inserted portion 2 may be employed that itself has a flatly expanding structure. FIG. 39A shows the inserted portion 2 tightly bundled so that it can pass through the guide sheath 6, and FIG. 39B shows the inserted portion 2 flatly expanded after it is projected from the opening 6a of the guide sheath 6.

Figure 40:
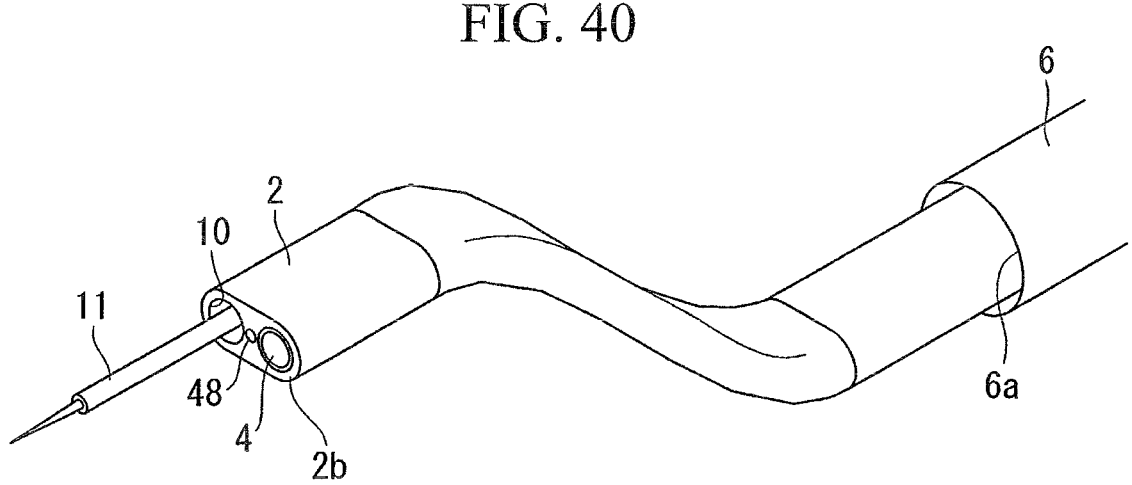
FIG. 40 is a partial perspective view showing an inserted portion of an endoscope, provided with another means for stabilizing the inserted portion relative to the pulsation of the heart.

Alternatively, an inserted portion 2 having a flat sectional shape may be employed, as shown in FIG. 40.

In the figure, reference sign 48 denotes an illumination light source.

Figure 41:
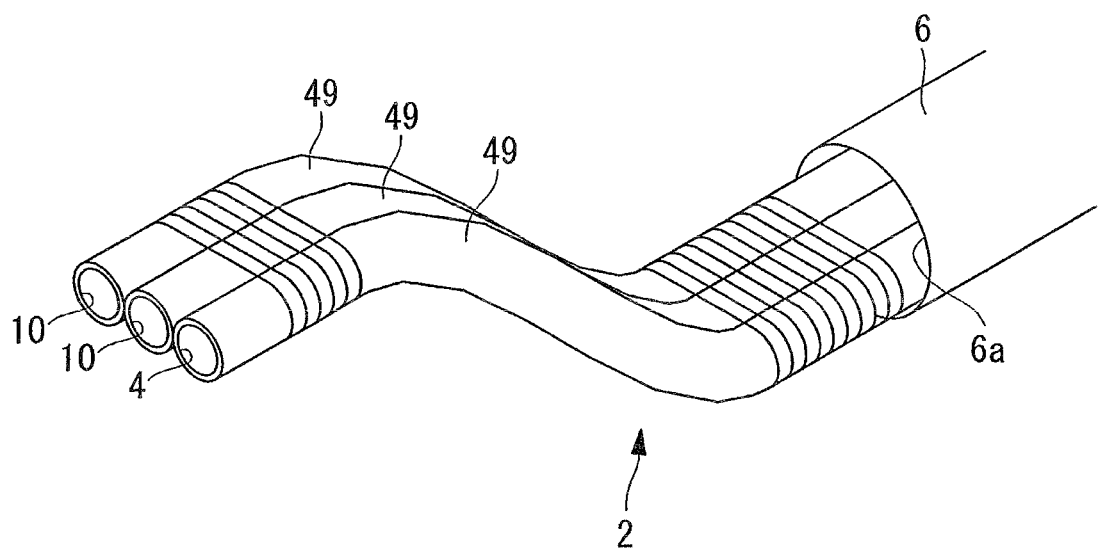
FIG. 41 is a partial perspective view showing an inserted portion of an endoscope, provided with another means for stabilizing the inserted portion relative to the pulsation of the heart.

Alternatively, as shown in FIG. 41, an inserted portion 2 may be employed that has a flat shape in which a plurality of tubular members having circular sections are arrayed in one line and bundled. In this case, preferably, the tubular members 49 include a tubular member having the observation optical system 4 and tubular members having channel exits 10.

Figure 42:
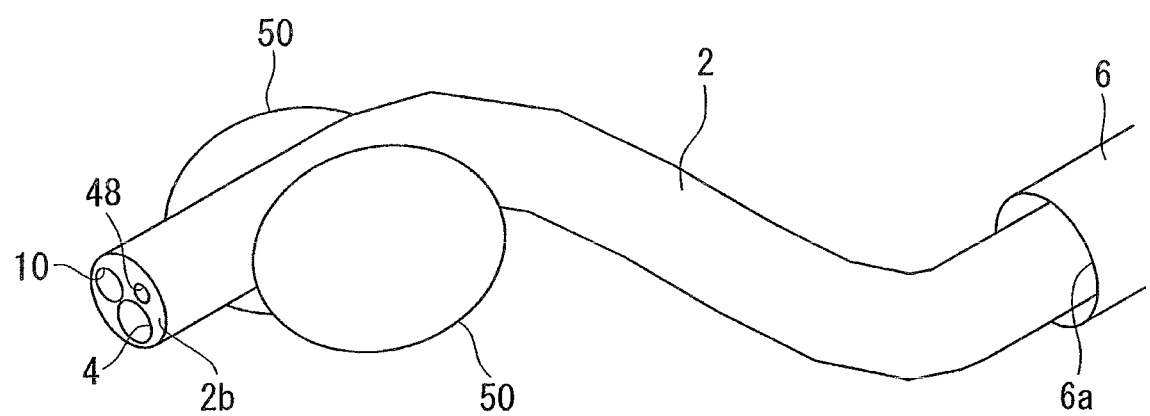
FIG. 42 is a partial perspective view showing an inserted portion of an endoscope, provided with another means for stabilizing the inserted portion relative to the pulsation of the heart.

Alternatively, as shown in FIG. 42, balloons 50 may be inflated from two circumferentially deviated positions of the inserted portion 2. Accordingly, since the surface of the heart A is pressed simultaneously by the balloons 50 at the two positions, it is possible to stably support the inserted portion 2 while suppressing pulsation of the heart A.

Figure 43:
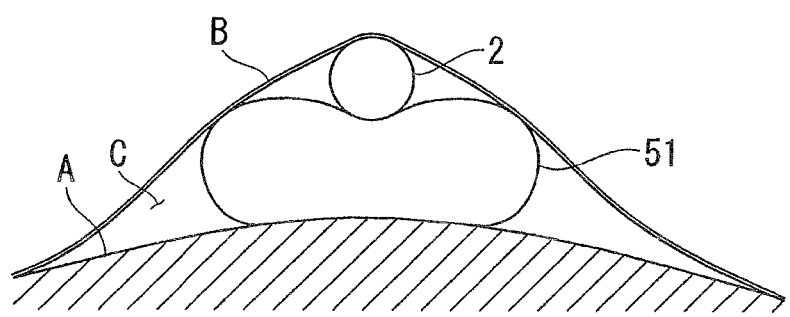
FIG. 43 is a cross-sectional view showing an inserted portion of an endoscope, provided with another means for stabilizing the inserted portion relative to the pulsation of the heart.

Alternatively, as shown in FIG. 43, the inserted portion 2 may be stabilized by employing a balloon 51 that expands into a shape having an elongated circular section.

The first and second embodiments have been described above in the context of examples where an endoscope according to the present invention is inserted between the heart and the pericardium to observe the heart. Alternatively, it is possible to insert an endoscope between other pairs of organs, for example, the lungs, the stomach, the gallbladder, the pancreas, the spleen, the intestines, the kidneys, the urinary bladder, the uterus, the peritoneum, the pleura, the thoracic diaphragm, between brain tissues, or between skeletal muscles to observe these organs. When an endoscope is inserted into a gap between mutually adjacent organs, since the endoscope is pressed by the organs on either side, it is difficult to provide a sufficient observation distance between the observation window and the organ surfaces. Particularly, when these organs adhere to each other, it is even more difficult to provide an observation distance. However, with an endoscope according to the present invention, even in the case of adhering organs, it is possible to provide an appropriate observation distance by a simple operation, allowing the surfaces of the organs to be readily observed.

What is claimed is:

1. An endoscopy method comprising:
an inserting step of inserting an inserted portion of an endoscope into a body;
a securing step of securing a distal-end portion of the inserted portion to a surface of a heart inside the body such that an observation window, which is provided on one of a side face of the inserted portion or on the distal-end portion, faces toward the surface of the heart; and
an observation-distance adjusting step of adjusting the distance between the observation window and the surface of the heart by inflating a balloon provided on a portion of the inserted portion, where the balloon is provided on less than a full circumference of the inserted portion, and the portion includes a side that the observation window faces.

2. An endoscopy method according to claim 1,
wherein in the inserting step, the inserted portion is inserted into a gap between the heart and the pericardium, and
wherein the endoscopy method further includes a space forming step of forming an observation space for the endoscope by widening the gap between the heart and the pericardium.

3. An endoscopy method according to claim 1,
wherein in the securing step, the inserted portion is secured to the heart at positions on both sides, along a lengthwise direction, of a curving portion provided at the inserted portion, and
wherein in the observation-distance adjusting step, the curving portion is curved.

4. An endoscopy method according to claim 1,
wherein in the inserting step, the inserted portion is inserted, which is pretrained into a shape curved at a predetermined curvature, in such a state that the inserted portion is extended to have a curvature smaller than the predetermined curvature, and
wherein in the observation-distance adjusting step, the inserted portion is released from the extended state to the predetermined curvature.

5. An endoscopy method according to claim 1, wherein in the observation-distance adjusting step, an elastic member is pressed in a lengthwise direction from a proximal-end of the inserted portion, the elastic member being disposed on a side face of the inserted portion along the lengthwise direction and fixed at a distal end of the inserted portion, thereby projecting the elastic member in a radial direction.

6. An endoscopy method according to claim 1, wherein in the observation-distance adjusting step, one end of a plurality of link members is moved in a lengthwise direction of the inserted portion, the plurality of link members being coupled so as to pivot with each other, thereby moving a joint portion in a radial direction.

7. An endoscopy method according to claim 1,
wherein in the securing step, the inserted portion is secured to the tissue by using a magnetic force, and
wherein in the observation-distance adjusting step, the magnetic force is adjusted to adjust a magnetic repelling force between the magnetic force and another magnetic force generated from the adjacent tissue.

8. An endoscopy method according to claim 1,
wherein in the securing step, the inserted portion is secured to the tissue by using a fluid jet, and
wherein in the observation-distance adjusting step, the flow velocity of the fluid jet is adjusted.

9. An endoscopy method according to claim 1, wherein in the inserting step, the inserted portion is inserted from under the xiphoid process into the gap between the heart and the pericardium.

10. An endoscopy method according to claim 1, wherein the inserted portion is operated under X-ray radiography.

11. An endoscopy method according to claim 1, wherein in the inserting step, the inserted portion is inserted between organs adhering to each other.

12. An endoscopy method according to claim 1, wherein, in the securing step, the distal-end portion of the inserted portion is attached to the heart by using a negative pressure.

13. An endoscopy method according to claim 9,
wherein in the securing step, the distal-end portion is secured to the heart or the pericardium, and
wherein in the observation-distance adjusting step, the gap between the heart and the pericardium is widened by freeing from the heart the distal-end portion secured to the heart or the pericardium.

14. An endoscope comprising:
a long, thin inserted portion that is inserted into the body of a patient;
securing means for securing the inserted portion to a tissue inside the body, the securing means being provided at least at a distal-end portion of the inserted portion;
an observation optical system that is provided at the inserted portion and that acquires an image of the tissue or adjacent tissue adjacent to the tissue; and
observation-distance adjusting means for adjusting the distance between the observation optical system and one of a surface of the tissue or a surface of the adjacent tissue,
wherein an observation window is provided on one of a side face of the inserted portion or on the distal-end portion, and
wherein the observation-distance adjusting means is provided on a portion of the inserted portion and the observation-distance adjusting means is provided on less than a full circumference of the inserted portion, where the portion includes a side that the observation window faces.

15. An endoscope according to claim 14, wherein the securing means includes an attachment unit that attaches to the tissue by using a negative pressure.

16. An endoscope according to claim 14, wherein the securing means includes one or more hook members that are hooked to the tissue.

17. An endoscope according to claim 14, wherein the securing means includes a balloon member that is inflated so as to be engaged with a recess of the tissue.

18. An endoscope according to claim 14, wherein the securing means includes forceps for holding the tissue.

19. An endoscope according to claim 14, wherein the observation-distance adjusting means is implemented by a balloon that is disposed between the tissue or the adjacent tissue and the inserted portion and that is inflated or deflated to adjust the distance between the observation optical system and a surface of the tissue or a surface of the adjacent tissue.

20. An endoscope according to claim 14,
wherein a plurality of the securing means are provided at intervals along a lengthwise direction of the inserted portion, and
wherein the observation-distance adjusting means is implemented by a curving portion that is disposed between the securing means and that curves the inserted portion.

21. An endoscope according to claim 14, wherein the observation-distance adjusting means is implemented by training the inserted portion into a curved shape.

22. An endoscope according to claim 14, wherein the observation-distance adjusting means is implemented by an elastic member that is disposed on a side face of the inserted portion along a lengthwise direction, that is fixed at a distal end of the inserted portion, and that is projected in a radial direction by being pushed in the lengthwise direction from a proximal end of the inserted portion.

23. An endoscope according to claim 14, wherein the observation-distance adjusting means is a link mechanism that includes a plurality of link members coupled so as to pivot with each other and that moves a joint portion in a radial direction when one end thereof is moved in a lengthwise direction of the inserted portion.

24. An endoscope according to claim 14, wherein the inserted portion has a channel for passing various instruments in accordance with procedures performed on the tissue or the adjacent tissue.

25. An endoscope according to claim 14, wherein the securing means is magnetic-force generating means for securing the inserted portion to the tissue by using a magnetic force.

26. An endoscope according to claim 14, wherein the securing means is fluid jetting means for securing the inserted portion to the tissue by using a fluid jet.

27. An endoscope according to claim 14, wherein the observation-distance adjusting means observes the tissue to which the inserted portion is secured by the securing means or a tissue in proximity to the tissue to which the inserted portion is secured.

28. An endoscope according to claim 15, wherein the attachment unit has an attachment surface for attachment to the tissue such that the angle of the attachment surface relative to the inserted portion is changeable.

29. An endoscope according to claim 15, wherein the attachment unit has a suction hole provided on a side face of the inserted portion.

30. An endoscope according to claim 15,
wherein a plurality of the attachment units are provided at intervals along a lengthwise direction, and
wherein the observation optical system is provided between a pair of the attachment units.

31. An endoscope according to claim 21, wherein the observation-distance adjusting means includes a guide sheath that accommodates the inserted portion in an extended state such that the inserted portion is projectable and retractable from a distal end of the guide sheath.

32. An endoscope according to claim 22, wherein the elastic member has a cross-sectional shape extending in a circumferential direction of the inserted portion.

33. An endoscope according to claim 22, wherein the elastic member is formed of a bundle of wires arrayed in the circumferential direction of the inserted portion.

34. An endoscope according to claim 24,
wherein the observation optical system is provided on a side face of the inserted portion, and
wherein the channel has an exit provided at a circumferential position substantially corresponding to the observation optical system.

35. An endoscope according to claim 24, wherein the channel has an exit provided so that an instrument projected from the exit passes through a field of view of the observation optical system.

36. An endoscope according to claim 25, wherein the observation-distance adjusting means includes magnetic-force adjusting means for adjusting the magnetic force generated by the magnetic-force generating means to adjust a magnetic repelling force between the magnetic-force generating means and another magnetic-force generating means provided in the adjacent tissue.

37. An endoscope according to claim 26, wherein the observation-distance adjusting means is flow-velocity adjusting means for adjusting the flow velocity of the fluid jetted by the fluid jetting means.

38. An endoscope according to claim 28, wherein the attachment unit includes an attachment pad having the attachment surface and a joint that joins the attachment pad with the inserted portion so that the attachment pad is pivotable about an axis perpendicular to a lengthwise axis of the inserted portion.

39. An endoscope according to claim 38, wherein the joint is a flexible tubular member that conveys a negative pressure to the attachment pad.

40. An endoscope according to claim 39, wherein the tubular member is bellows.

* * * * *